United States Patent [19]

Lodder

[11] Patent Number: 5,164,597
[45] Date of Patent: Nov. 17, 1992

[54] METHOD AND APPARATUS FOR DETECTING MICROORGANISMS WITHIN A LIQUID PRODUCT IN A SEALED VIAL

[75] Inventor: Robert A. Lodder, Lexington, Ky.

[73] Assignee: University of Kentucky Research Foundation, Lexington, Ky.

[21] Appl. No.: 696,354

[22] Filed: May 6, 1991

Related U.S. Application Data

[63] Continuation-in-part of Ser. No. 581,823, Sep. 12, 1990, which is a continuation-in-part of Ser. No. 414,799, Sep. 29, 1989, abandoned.

[51] Int. Cl.$^5$ ............................................. G01N 21/51
[52] U.S. Cl. .................................... 250/341; 250/228; 250/574; 356/338; 356/341
[58] Field of Search ............... 250/341, 574, 228, 343; 356/337, 338, 341, 343

[56] References Cited

U.S. PATENT DOCUMENTS

| | | | |
|---|---|---|---|
| 3,627,424 | 12/1971 | Dorman et al. | 356/338 |
| 3,966,332 | 6/1976 | Knapp et al. | 250/223 B |
| 4,087,184 | 5/1978 | Knapp et al. | 250/223 P |
| 4,118,625 | 10/1978 | Underwood | 250/343 |
| 4,278,887 | 7/1981 | Lipshutz et al. | 250/432 R |
| 4,291,983 | 9/1981 | Kraft et al. | 250/574 |
| 4,804,273 | 2/1989 | Tondello et al. | 250/574 |
| 4,900,923 | 2/1990 | Gerlinger | 250/228 |

Primary Examiner—Carolyn E. Fields
Attorney, Agent, or Firm—King & Schickli

[57] ABSTRACT

An apparatus and method are provided for the noninvasive and nondestructive detection of microorganisms within a liquid product contained within a sealed vial. The apparatus includes a near-IR light source that produces both incident and reference beams having a wavelength between 800 and 2500 nm and, more preferably, 1100 and 1360 nm. The apparatus also includes an integrating sphere having incident and reference beam ports and a sample window opposite the incident beam port. A detector is mounted in the integrating sphere substantially adjacent the sample window. A substantially U-shaped mirror is provided to hold the vial. The U-shaped mirror is of a size substantially corresponding to the diameter of the vial. In operation, the incident beam is directed through a sample window so as to enter the vial adjacent a sidewall of the mirror. In this way the U-shaped mirror reflects the incident beam so that it passes through the vial three times before returning to the detector. A computer analyzes the resulting signals from the detector.

19 Claims, 19 Drawing Sheets

METHOD AND APPARATUS FOR DETECTING MICROORGANISMS WITHIN A LIQUID PRODUCT IN A SEALED VIAL

This application is a continuation-in-part of U.S. patent application Ser. No. 07/581,823 filed Sep. 12, 1990 which is a continuation-in-part of U.S. patent application Ser. No. 07/414,799, now abandoned, filed Sep. 29, 1989.

BACKGROUND OF THE INVENTION

Biotechnology has created a number of new and potentially life-saving products. Many of these products cannot withstand exposure to the digestive tract as an oral formulation and must instead be formulated as injectables. Furthermore, these molecules may not survive terminal sterilization by autoclaving. In these cases, an aseptic-filling process is required although it is a less reliable sterilization method, making detection of unsterile products a necessary task. Conventional microbiology methods and turbidimetry are currently employed as inspection techniques to assess sterility. However, these procedures are typically very time consuming, invasive, and characteristically provide relatively low sensitivity and as such may not detect low levels of contamination.

In more detail, many drugs must be formulated as parenteral products (injectables), and delivered in a solution contained in a sterile vial or intravenous (IV) bag. Maintaining the stability of the drug (preventing decomposition) and insuring the sterility of the drug (absence of microbial growth) can be a problem.

Preservative systems and sterilization procedures for parenteral products must be well monitored (see Henry L. Avallone, *J. Parenter. Sci. Technol.* 1985, 39(2), 75–79) and tested by validated microbiological methods (see "Validation of Steam Sterilization Cycles", Technical Monograph No. 1, and "Validation of Aseptic Filling For Solution Drug Products", Technical Monograph No. 2, Parenteral Drug Association, Inc., 1980). The typical method of assuring the sterility of vials and IV bags is to fill them with the desired product and sterilize the final filled product by autoclaving (see John Y. Lee, *Pharmaceutical Technology* 1989, 13(2), 66–72). Unfortunately, the autoclaving process can also stress fragile molecules and denature proteins. In such cases, the IV bag or vials are filled aseptically (under conditions that are as sterile as possible) and sterilized by filtration with a 0.2 μm filter. The product can then be used.

Unfortunately, sterility by aseptic filling is not as certain as with terminal sterilization (autoclaving). It has been estimated that terminal sterilization by autoclaving results in a sterility assurance level of $10^{-6}$ or better (probability of an unsterile unit), while aseptic filling generally achieves an assurance level of only $10^{-3}$ or one contaminated unit per thousand (see *Quality Control Reports: The Gold Sheet*, in F-D.C. Reports, Bill Paulson, Ed., 1988, 22(3), 1–6 and Henry L. Avallone, J. Parenter. Sci. Technol. 1986, 40(2), 56–57). Because of this difference in sterility assurance levels, the FDA is requiring manufacturers who produce aseptically-filled products to submit methods and data justifying why terminal sterilization cannot be used. The manufacturer must also describe the microbiological monitoring and control procedures used to assure sterility (see FDA Guideline on Sterile Drug Products Produced by Aseptic Processing; Food and Drug Administration, Rockville, Md., July, 1987).

The challenge to the analyst is to determine which product is contaminated and to prevent its use, assuring that the final occurrence of defective units is very low. Perhaps the simplest method of assuring product sterility involves the incubation of an IV bag or vial until any microorganisms that might be present grow sufficiently numerous that turbidity develops. The turbidity is then detected by ordinary optical methods or by visual examination. Also, microscopic examination would reveal the identity of the contaminating microorganism(s). Unfortunately, it can take a significant amount of time for turbidity to develop, and products contaminated with small amounts of microorganisms such as bacteria, molds, or yeast might not show visible turbidity. Furthermore, some IV bags or vials are composed of materials that interfere with the visible detection of turbidity.

U.S. Pat. No. 4,367,041 to Webb teaches a liquid chromatography method where pure components of a mixture may be separated during chromatography by measurement of the ratio of absorbance at two wavelengths.

A system for detecting the tampering with capsules using near-infrared (near-IR) light is described by Robert A. Lodder et al. in *Anal. Chem.* 1987, 59, 1921–1930. Near-IR methods are commonly applied to the analysis of aqueous samples, see Robert A. Lodder et al., *Appl. Spectrosc.* 1988, 42, 518–519 and have been used in the detection of contaminated products, see Robert A. Lodder et al., *Appl. Spectrosc.* 1988, 42(4), 556–558.

An analytical method that would enable the detection of low levels of microorganisms in parenteral products without the need for incubation for a long period of time would represent a significant advance in the analysis of parenteral products. Such a method would preferably be used to detect contamination by bacteria, yeast, or molds in drug vials and IV bags.

SUMMARY OF THE INVENTION

The present invention comprises an analytical method based on near-IR light intensity changes e.g., light scattering or absorption, as a method for detecting small quantities of microorganisms in drug products e.g., in sealed bags or vials. The method is, advantageously, noninvasive and nondestructive, preventing possible contamination of bag or vial units by the analytical method itself. In contrast, in prior art procedures sterility testing and microbial identifications are accomplished by looking at only a small number of units from the total lot of a product. This is because these prior art microbiological tests are, time consuming, laborious, invasive, and in essence destroy the product that is being examined.

Near-IR light back-scattering is used in the present method for determining low levels of contamination noninvasively and nondestructively. The method is used to detect contamination by yeast, mold, and/or bacteria with a detection limit potentially as low as three cfu of yeast per mL. Using the near-IR method of the invention, each container, e.g. IV bag or vial, can be evaluated intact with its sterility maintained, allowing the products to be used or evaluated by another method.

The apparatus of the present invention includes a vial holder having a substantially U-shaped mirror. The U-shaped mirror has a width substantially corresponding to but slightly greater than the diameter of the vial to be tested and held therein. The apparatus also includes a near-IR light source that produces both incident and reference beams having a wavelength of 800–2500 nm and, more preferably, 1100–1360 nm. The light source is operatively connected by fiber optics to an integrating sphere. The integrating sphere has both reference and incident beam ports as well as a sample window directly opposite the incident beam port. A detector is also mounted in the wall of the integrating sphere adjacent the sample window. In operation, the incident beam is directed through the sample window so as to enter the vial adjacent a sidewall of the mirror. In this way, the U-shaped mirror reflects the incident beam so that it passes through the vial and its contents three times before returning to the detector. Any solid contaminants, such as microorganisms, present in the liquid product held in the vial serve to scatter the incident beam. The scattered light is collected by the inner reflective wall of the integrating sphere and focused on the detector. Similarly, the reference beam is also focused on the detector. Signal values from the detector are then recorded and analyzed by computer and the resulting spectral patterns are compared with patterns of known standards to determine the existence, extent and/or type of contamination present.

Figure 1:
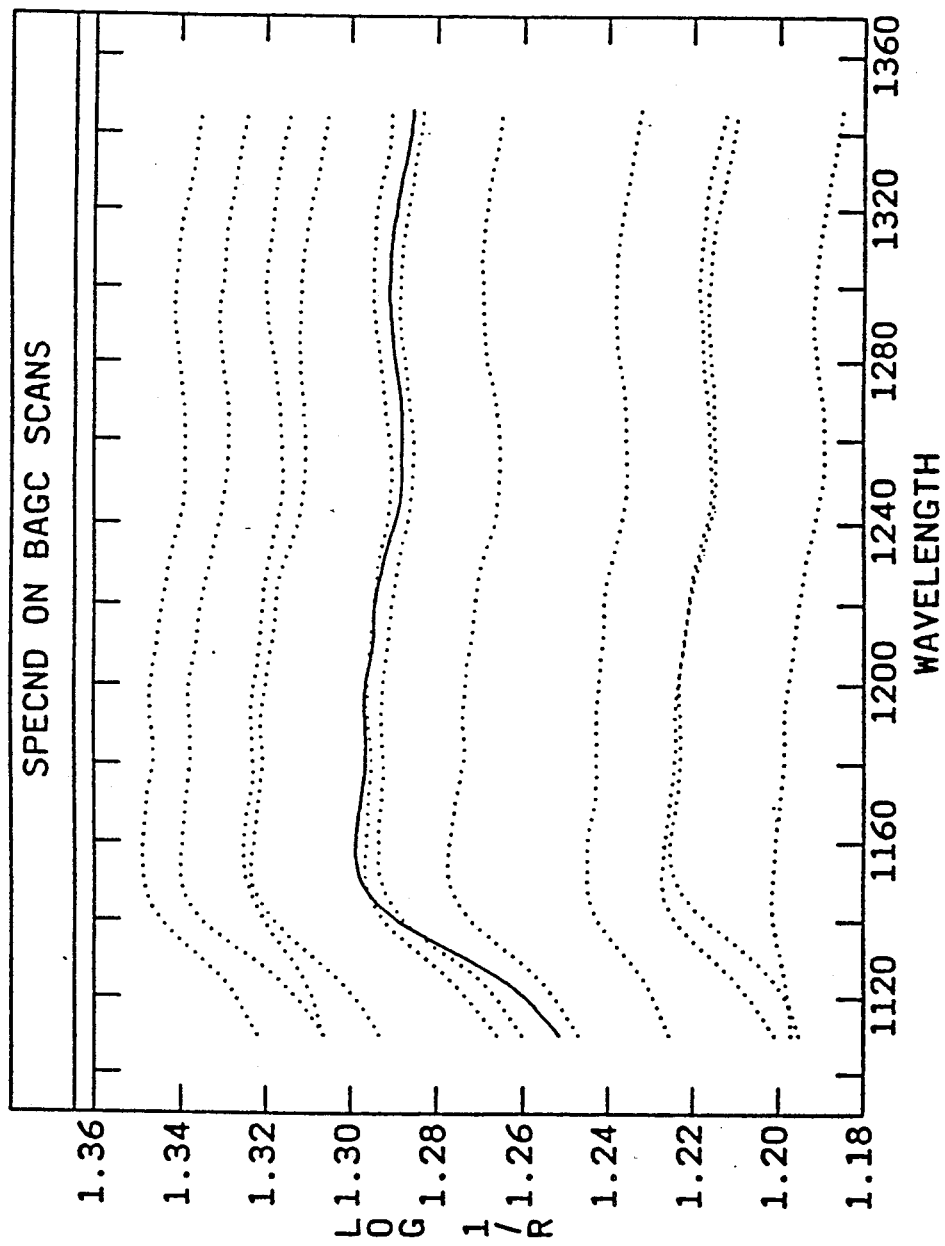
FIG. 1 depicts 11 traces of the near infrared spectra of a PVC IV bag containing 5% dextrose injection USP and 0.5 mg per mL of ranitidine as the hydrochloride. The "log 1/R" indicates the logarithm of the reciprocal of the reflectance intensity of the radiation.

Reference will now be made in detail to the drawing Figures.

DETAILED DESCRIPTION OF THE INVENTION

As used in the present specification, a near-IR spectrum is a spectrum of the scattering (or reflectance) of light introduced into a liquid sample. This is a physical phenomenon and is, in effect, a deflecting of the incident near-IR light. Such is not an absorbance or transmittance spectrum as in the more typical IR spectra which are indicative of the individual chemical structural features, of a chemical compound. Since the scattering method of the invention depends on the amount of scattered (or reflected) light, any absorbance in the liquid sample will decrease the quantity of light available for scattering.

The present invention comprises a method for the detection of microorganisms in a liquid sample to be tested, which comprises the steps of obtaining a near-IR spectrum of the liquid sample and then comparing the spectrum to a standard sample. In more detail, the detection of microorganisms will often be for the purpose of determining sterility (or the lack of sterility) in the liquid sample. Examples of microorganisms include any living cells which are individually not detected by visual inspection. Specific examples include yeast, bacteria or mold. The liquid sample to be tested is, in particular, water or an aqueous IV solution such as a solution of dextrose, typically 5% (w/v), or isotonic sodium chloride solution e.g., about 0.9% w/v. Other liquid samples that can be evaluated according to the method of the present invention include aqueous solutions used as growth media for fermentation stock or the growth of other cells. In this case, one would detect the presence and quantity of cells in order to determine whether or not there is sufficient population of the cells for the purpose intended. In contrast, if the method of the present invention were used to determine sterility, the object of the exercise would be to confirm whether or not the liquid sample is sterile as indicated by the absence of microorganisms.

Typical microorganisms to be detected according to the method of the present invention include yeast, bacteria and mold. Other cells include algae and other living cell lines such as cancer cell lines.

The infrared spectrum to be taken according to the method of the present invention is a spectrum in the range of about 800–2500 nanometers (nm), more particularly 1100–1360 nm. The spectrum can be taken on any conventional near-IR spectrophotometer such as the InfraAlyzer 500 from Bran+Luebbe of Elmsford, N.Y., the 6500 spectrophotometer from NIR Systems of Silver Spring, Md. and the Quantum 1200 spectrophotometer from LT Industries of Silver Spring, Md. In particular, the InfraAlyzer 500 can be used according to the method of the present invention because it is a double beam instrument and therefore need not be corrected for variations such as fluctuations in source intensity.

The near-IR spectrophotometer utilized is configured to detect scattering of the incident beam or changes in back-reflected light intensities because of absorption processes. Detection of scattered or back-reflected light from the incident beam can be accomplished by installing equipment for light scattering as known in the art. For example, the EDAPT-1 probe, available from Bran+Leubbe is suited for this purpose. Adaptation of commercially available near-infrared spectrophotometers for the detection of scattered light is described by Robert A. Lodder et al. in *Appl. Spectrosc.* 1988, 42, 518–519 and in *Appl. Spectrosc.* 1988, 42(4), 556–558. Other methods for detecting light scattering to be used in the method of the present invention are those described in the chapter entitled "Molecular Scattering Methods" in *Spectrochemical Analysis* by James D. Ingle and Stanley R. Crouch, pp. 494–524, Prentice Hall, Englewood Cliffs, N.J., 1988.

The liquid sample to be tested according to the invention is, in particular, held in a container which is at least partially transparent to at least one wavelength of near-infrared light. As the spectrophotometer scans the near-infrared spectrum at those wavelengths wherein both the liquid medium and the container holding the medium are at least partially transparent, the spectrophotometer will then detect changes in the light that passes through the container and medium and is reflected back or scattered due to the presence of the microorganism to be detected. Examples of the container include bags, bottles, tubes, vials and ampules of glass (e.g., high grade borosilicate glass) or an organic polymer (e.g., PVC, polyethylene and CR3 polymer from Abbott Laboratories, Chicago, Ill.). In particular, the method of the invention can be used to detect the sterility or loss of sterility, being more precise, of a liquid for parenteral administration to humans. Examples of parenteral administration include IV and intramuscular injections or irrigation of a wound or other body cavity. The liquid medium may be composed of only a fluid for administration or it may contain a pharmaceutical formulation such as ranitidine hydrochloride injection. In addition to checking the sterility of an aseptically refilled container, wherein a concern is the growth of microorganisms, the method of the present invention can also be used, conversely, to check the presence of such microorganisms that are beneficial e.g., wherein one would want to check that the growth of bacteria in a fermentation broth had been proceeding satisfactorily. A particular application of the present invention is the determination of sterility in an aseptically-filled container adapted for administration of its contents to a human.

Once the spectra for the test sample and standard ("training") samples are obtained, the spectra are compared. Comparison may be by visual inspection of the spectra (e.g., in the range of 1100–1360 nm by measuring the log of the reciprocal of reflectance). In general, several e.g., 10 spectra will be taken for each sample at various locations through the container. The trace of each of the spectra of the negative log of reflectance (or the log of the reciprocal of reflectance) are considered. With a liquid sample having an absence of microorganisms e.g., a sterile product, the various traces of the spectra taken at different portions of the container will, in general, have the same shape. In contrast, traces of a product with microorganisms present will show different shapes for the spectra when taken through different portions of the container. In fact, the traces will often cross and such crossing is a good indicator of the presence of microbial contaminants.

Figure 2:
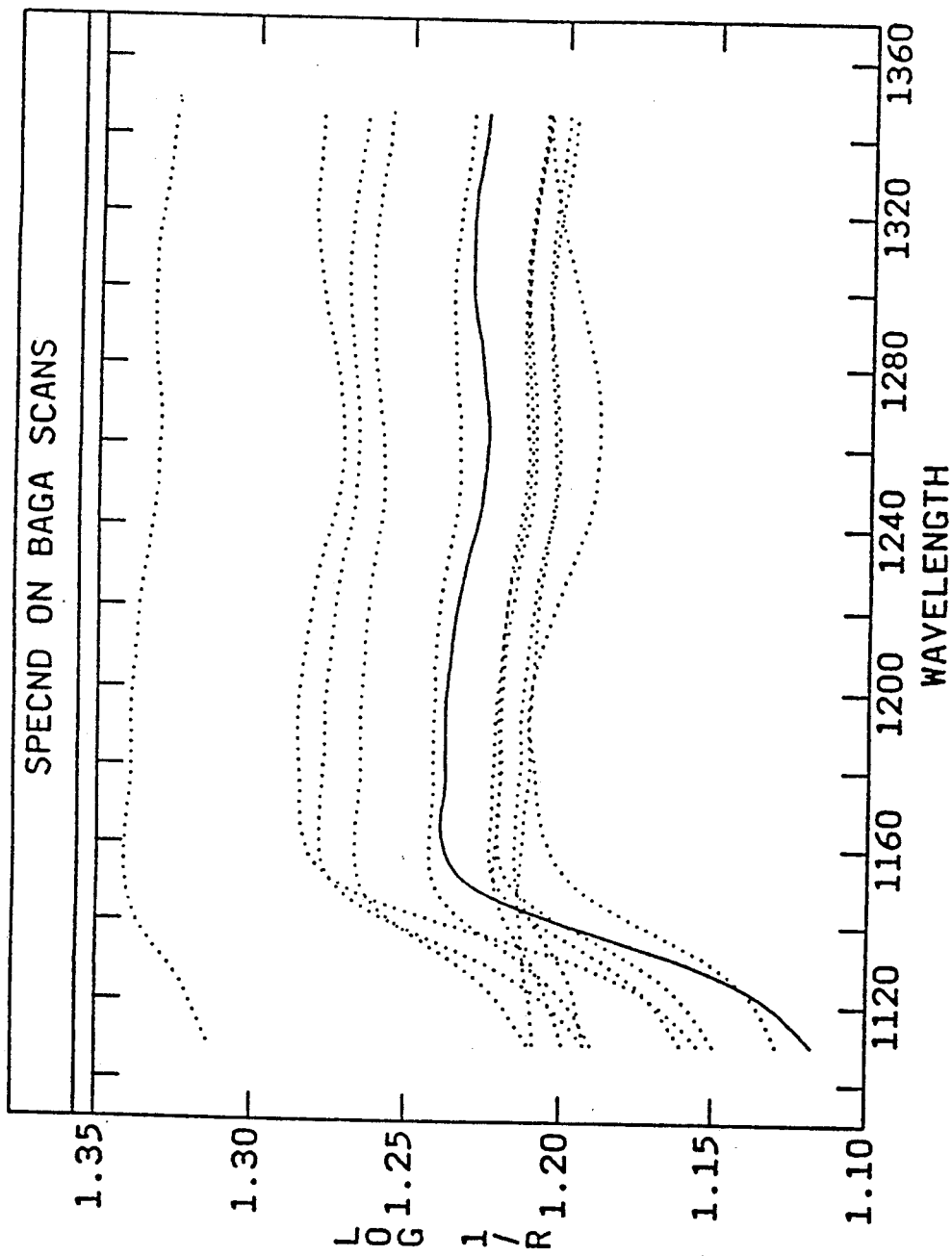
FIG. 2 is a depiction of 11 separate spectra as set forth in FIG. 1 with the exception that the IV bag of 5% dextrose solution USP and 0.5 mg per mL ranitidine has been contaminated with *Pseudomonas aeruginosa* (ATCC No. 9027).
Figure 3:
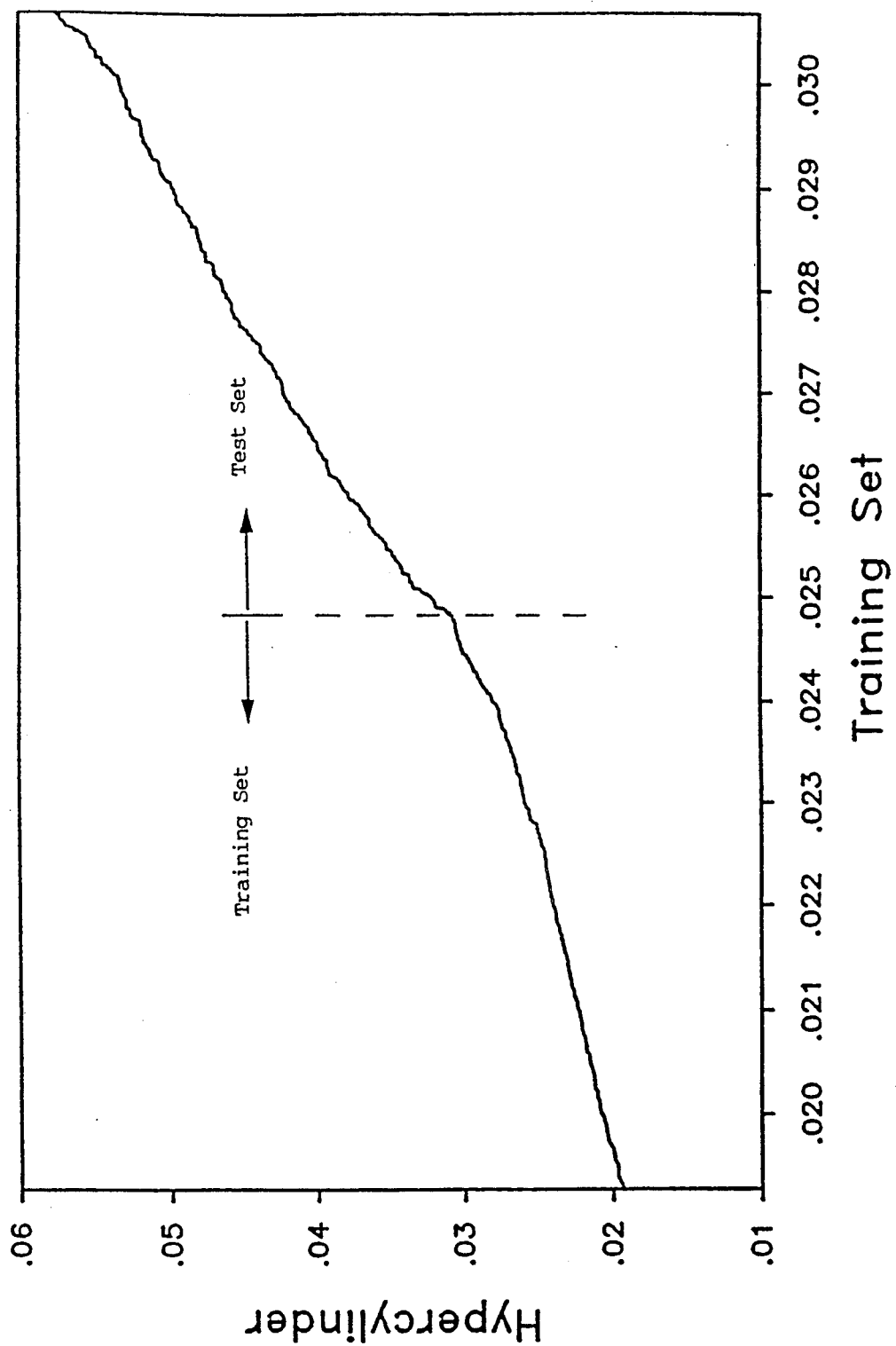
FIG. 3 is the most common appearance of a QQ plot of the training set (the points on the left half of the plot) and the test set (the points on the right half of the plot).

For example, in FIG. 1, one can see that the traces of spectra at various portions of the sample are nearly identical to each other with the only difference essentially being the position of the trace on the spectra as caused by differences in the pathlength at the particular position at which the spectrum was taken. In FIG. 2, one can see that contamination caused by microorganisms (bacteria in this case) results in traces crossing at various positions. This crossing phenomenon can be used to determine the presence of microorganisms.

An analysis of the distribution quantiles of near-IR spectral data (Robert A. Lodder et al. in *Appl. Spectrosc.* 1988, 42(8), 1512–1520) provides a powerful means of interpreting light-scattering results. The principal advantage of the near-IR light-scattering method is that every single unit of the product can be examined for sterility without invading and destroying the product. Furthermore, the method appears able to differentiate between different types of microorganisms in solution as well as to isolate the location of the organisms inside the container and determine the number of microorganisms present.

The determination of microorganisms according to the invention is based predominantly upon scattering of near-IR light by solid objects inside the container, e.g. sealed IV bag or vial. Monochromatic near-IR light is directed into the sample, and the solid material in the sample scatters light back into an integrating sphere for collection and detection. A fiber-optic diffuse-reflectance probe is used to collect spectral data from a near-IR beam with a wavelength range from 1100–1360 nm. Light is directed into the sample from a fiber-optic bundle that is placed in the integrating sphere, e.g. a one-inch gold sphere directly opposite the sample window (or beam port). A reference fiber-optic bundle is also present to direct near-IR light into the integrating sphere (reference beam). In particular, one may use such a pseudo-double-beam configuration to compensate for noise caused by bending of the fiber and by source intensity variations. Signal values are recorded as a ratio of intensities between the sample and reference beams. The logarithm of the reciprocal of the reflectance intensity recorded by this method is transmitted to a computer such as a MicroVAX II for analysis.

EXAMPLE 1

Equipment. The spectrometer used to generate the near-IR light that was transmitted through the optical fibers was in InfraAlyzer 500 scanning spectrophotometer (Bran-Leubbe, Inc., Elmsford, N.Y.). The data were actually collected on an IBM PS/2 model 50 computer (IBM Corp., Armonk, N.Y.) running IDAS software (Bran+Leubbe). The collected reflectance values were then transferred to a MicroVAX II computer system (Digital Equipment Corp., Maynard, Mass.) and an IBM 3090-300E vector supercomputer. Spectral data were processed in Speakeasy IV Epsilon (Speakeasy Computing Corp., Chicago, Ill.) programs that were written specifically for this purpose.

Materials. Thirty PVC IV bags containing 5 dextrose injections USP (Viaflex 150-mL containers, Lot# C092445, Baxter Healthcare Corp., Deerfield, Ill.) were injected with 3-mL of Zantac injection 25 mg/mL ranitidine as the hydrochloride, Glaxo Inc., Research Triangle Park, N.C.). Bags were injected through the additive port with a sterile disposable syringe and 21G×1.5 in. needle (Becton Dickinson, Rutherford, N.J.). The nominal ranitidine concentration in each bag was 0.5 mg/mL.

The microorganisms injected into the bags included: *Candida albicans* (American Type Culture Collection number 10231), *Aspergillus niger* (ATCC no. 16404), and *Pseudomonas aeruginosa* (ATCC no. 9027). These microorganisms were chosen to include a species of yeast, mold, and bacteria, respectively, which are typically tested to meet USP and FDA requirements.

The inoculum was prepared by transferring the respective microorganism from a lyophilized culture onto a solid agar medium and incubating at suitable temperatures for sufficient growth. For *Pseudomonas aeruginosa*, Trypicase Soy Agar was used, and the incubation time was 18-24 hours. Sabouraud Dextrose Agar was used for *Candida albicans* and *Aspergillus niger* with incubation times of 40-48 hours and 7 days, respectively. These agars and incubation times are consistent with harvesting procedures for pharmaceutical microbiological assays (see "Preparation of Inoculum", Section <51>, USP XXII, United States Pharmacopeial Convention, 1989).

Cells were harvested into a sterile conical tube with 5% Dextrose Injection USP instead of sterile saline TS to be consistent with the diluent used in the IV bags. Cell concentrations for each species were adjusted to a target range of 10-100 cfu per 0.10 mL (100-1000 cfu/mL) using 5% Dextrose Injections USP. This range was selected to give a starting target concentration of approximately 1 cfu/mL per bag, which represents a reasonable contaminant load for a sterility violation. The number of cfu per mL in the inoculum of each species was determined in quadruplicate by the spread-plate method. The average inoculum concentrations from four plates were 1650 cfu/mL, 100 cfu/mL, and 120 cfu/mL for *Pseudomonas aeruginosa*, *Candida albicans*, and *Aspergillus niger*, respectively.

The additive port of each of the 30 bags was injected with 0.20 mL of inoculum from one of the three microorganisms (10 bags of each type). The bags were inverted several times to distribute cells throughout the bag.

Data Analysis. A spectral training set was constructed for each group of 10 bags containing a single variety of microorganism. The spectral training set was collected immediately after injection of the microorganisms. Spectra were also obtained from the bags before injection of the microorganisms. These spectra, however, were not used as the training set because the near-IR method appeared to detect the injection of medium and microorganisms, which results in a large disturbance in the spectra. All ten bags containing the same organisms were inoculated sequentially prior to the training-set scans. The time lag between the scanning of the first bag and tenth bag was approximately one hour. Furthermore, 12 scans over the wavelength range from 1100-1360 nm were taken from each bag at different portions of the bag. Therefore, each training set consisted of 10 IV bags containing one of three microorganisms in a 5% dextrose solution with drug. Twelve scans were taken from each bag so that each of the three training sets contained 120 spectral scans. During spectral analysis, a spectrum recorded at 130 wavelengths in the 1100-1360 nm region was projected as a single point in a 260-dimensional hyperspace. Thus, each training set was composed of a cluster of 120 points in a 260-dimensional hyperspace. The analytical procedure located the center of the training set from the spectra recorded at time-zero in a 260-dimensional space and integrated outward steadily in all directions in space from the center of this training set to the "edges" of the training-set cluster (the edges are defined typically as being three multidimensional standard deviations away from the center). This integral forms a function that is compared to a second integral, which is determined by integrating from the center of the combined training set and test set of spectra (where the test set is the spectra of the same group of IV bags as the training set although at a later time, such as 6, 12, 24 or 48 hours after the injection of microorganisms). The 260-dimensional points from these test-set bags scanned at the later times are projected into the same space as the training set spectra to form an augmented spectral cluster. Integrating from the center of the augmented set out in all directions at a constant rate produces a second integral. A plot of the first integral versus the second integral is used to form a QQ plot.

Figure 4:
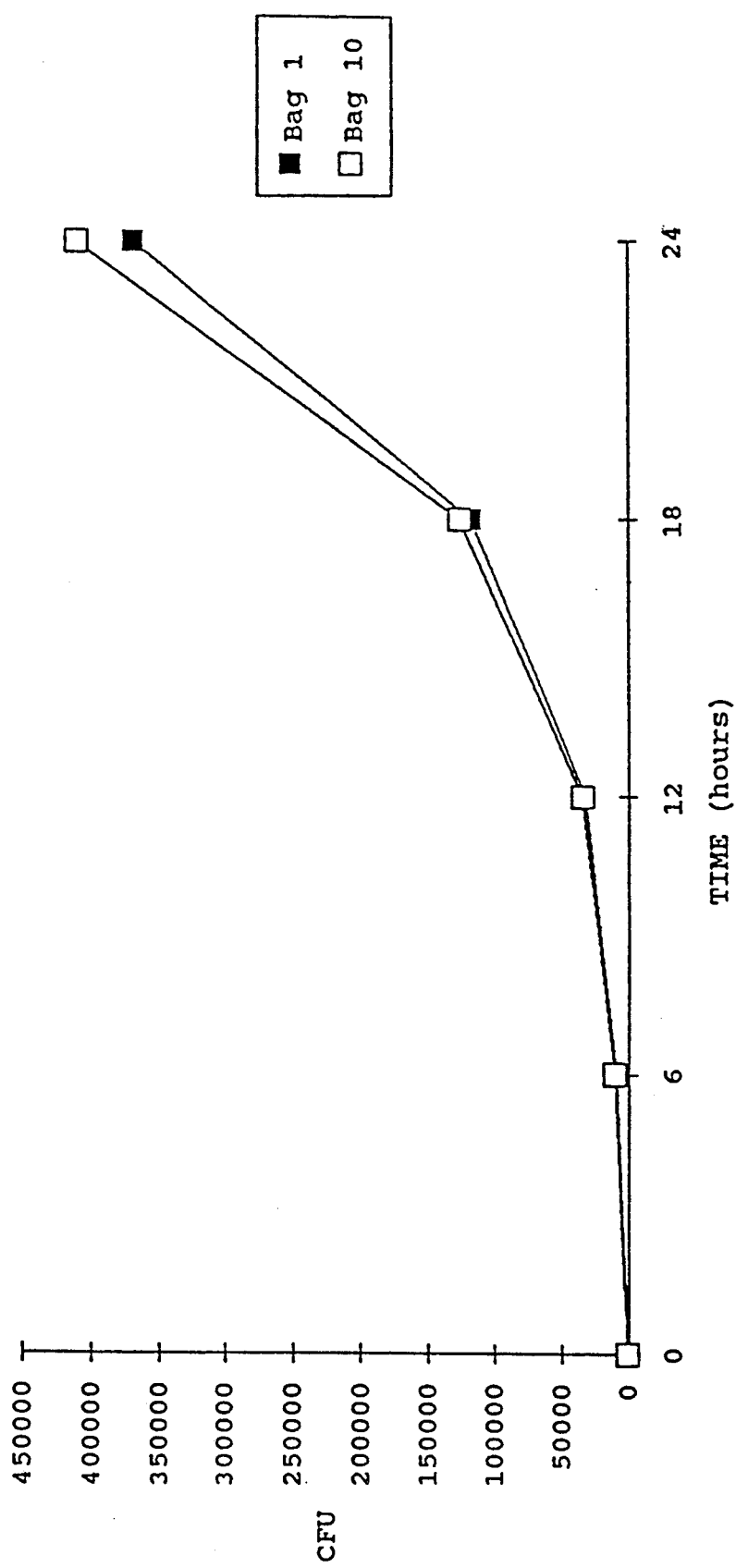
FIGS. 4, 5, and 6 depict the typical growth measured in cfu for a standard bacteria, yeast and mold, respectively, in 150-mg/mL ranitidine as the hydrochloride.

Microorganism concentrations in bags 1 and 10 from each group were measured at 0, 6, 12, 18 and 24 hours by removing 0.40 mL of solution from each bag with a 0.5 mL syringe. A 0.10-mL aliquot (or diluted aliquot at high microbiological concentrations) was transferred to each of four plates to determine the average cell concentration in cfu/mL. Trypticase Soy Agar was used as a growth medium for *Pseudomonas aeruginosa* aliquots, colonies were counted after 48 hours at 30°-35° C. The results of the counts are shown in FIG. 4. Sabouraud Dextrose Agar was used as the growth medium for *Candida albicans* and *Aspergillus niger* aliquots, and colonies were counted after 72 hours and 7 days, respectively, at 20°-25° C. These data are presented in graphical form in FIGS. 5 and 6.

Calculations. Spectral data were collected at wavelengths $N_{(m)} = \{1, 2, \ldots, w\}$ on each sample bag. Treatment of collected spectral data I begins with a smoothing process designed to reduce spectral noise:

$$I_{(1)} = W(W(I)) \qquad eq\ 1$$

where W represents a linear smoothing operation in which $i_{ij} = (i_{ij-2} + i_{ij-1} + i_{ij} + i_{ij+1} + i_{ij+2})/5$. Calculation of the first derivative of the smoothed spectra removes baseline variations from the spectra of the bag:

$$I_{(d1)i} = \left| \frac{dI_{(1)i}}{dN_{(m)}} \right| \qquad eq\ 2$$

A region of interest (i.e., a wavelength region where scattering is expected to be observed from cells) is then selected in the spectra of each bag. The region in this work encompasses one-third of the recorded wavelength spectrum, leading to $s_{(t)} = [w/3]$. A separate set of derivative spectra is then calculated for the region of interest:

$$I_{(d2)i} = \left| \frac{dI_{(1)i}\{st, st+1, st+2, \ldots d\}}{dN_{(m)}\{st, st+1, st+2, \ldots d\}} \right| \qquad eq\ 3$$

The two spectra from each bag that show the most distinguishing spectral features are selected by: The distinctive spectra, $H_{(1)}$ and $H_{(2)}$, are combined by:

$$I_{(s1)i} = \sum_{j=1}^{d} i_{(d1)ij} \quad \text{eq 4}$$

$$I_{(s2)i} = \sum_{j=1}^{d} i_{(d2)ij} \quad \text{eq 5}$$

$$P_1 = M(I_{(s1)}, \{1, 2, \ldots, u\}) \quad \text{eq 6}$$

$$P_2 = M(I_{(s2)}, \{1, 2, \ldots, u\}) \quad \text{eq 7}$$

$$H_{(1)j} = I_{(1)p1j} \quad \text{eq 8}$$

$$H_{(2)j} = I_{(1)p2j} \quad \text{eq 9}$$

The distinctive spectra, $H_{(1)}$ and $H_{(2)}$, are combined by:

$$H_{(1)j} = H_{(1)\{w, w-1, w-2, \ldots, 1\}} \quad \text{eq 10}$$

$$\phi = H_{(1)u} - H_{(2)1} \quad \text{eq 11}$$

$$H_{(2)j} = H_{(2)j} + \phi \quad \text{eq 12}$$

$$T_i\{1, 2, \ldots, u\} = H_{(1)j} \quad \text{eq 13}$$

$$T_i\{u-1, u+2, \ldots, 2u\} = H_{(2)j} \quad \text{eq 14}$$

$$T_i = W(T_i) \quad \text{eq 15}$$

to form an augmented spectral matrix that is useful in quantitative and qualitative analysis. The augmented space T thus has $d = 2u$ dimensions (columns) with one row for each sample bag.

Generally, another m-by-d matrix V, containing validation samples, is also assembled from the same source as the training set and is likewise treated in accordance to equations 1–15. The sample set V serves as an indicator of how well the training set describes its overall population variation. New spectra of sample bags under test are denoted X and are also treated in accordance to equations 1–15 before quantitative or qualitative analysis.

Bootstrap distributions are calculated by an operation $\kappa$; and $\kappa(T)$, $\kappa(X)$, and $\kappa(V)$ are each calculated in this manner. The results are the m-by-d arrays B, $B_{(x)}$, and $B_{(v)}$. The operation $\kappa(T)$, for example, begins by filling a matrix P with sample numbers to be used in bootstrap sample sets $B_{(s)}$:

$$P = P_{ij} = r \quad \text{eq 16}$$

The values in P are scaled to the training-set size by:

$$P = [(n-1)P + 1] \quad \text{eq 17}$$

A bootstrap sample $B_{(s)}$ is then created for each row i of the m-by-d bootstrap distribution B by:

$$B_{(s)} = t_{kj} \quad \text{eq 18}$$

where $\kappa$ are the elements of the i-th rows of P. The q-th row of B is filled by the center of the q-th bootstrap sample, $$b_{qj} = \sum_{i=1}^{n} b_{(s)ij}/n \quad \text{eq 19}$$

and the center of the bootstrap distribution is:

$$c_j = \sum_{i=1}^{m} b_{ij}/m \quad \text{eq 20}$$

The operation $\kappa$ is then repeated using X and V.

The multivariate data in the bootstrap distributions are then reduced to a univariate form:

$$s_{(T)i} = \left( \sum_{j=1}^{d} (b_{ij} - c_j)^2 \right)^{\frac{1}{2}} \quad \text{eq 21}$$

$$s_{(V)i} = \left( \sum_{j=1}^{d} (b_{(V)ij} - c_j)^2 \right)^{\frac{1}{2}} \quad \text{eq 22}$$

$$s_{(X)i} = \left( \sum_{j=1}^{d} (b_{(X)ij} - c_j)^2 \right)^{\frac{1}{2}} \quad \text{eq 23}$$

and these distances are ordered and trimmed according to a trimming-index set:

$$P(T) = \{mp+1, mp+2, mp+3, \ldots, m-mp\} \quad \text{eq 24}$$

to reduce the leverage effects of isolated selections at the extremes of the bootstrap distributions. Cumulative Distribution Functions (CDFs) for QQ plotting are formed by:

$$C_{(t)} = \partial(S_{(T)P(T)}, S_{(T)P(T)}) \quad \text{eq 25}$$

$$C_{(x)} = \partial(S_{(T)P(T)}, S_{(X)P(T)}) \quad \text{eq 26}$$

$$C_{(V)} = \partial(S_{(T)P(T)}, S_{(V)P(T)}) \quad \text{eq 27}$$

Graphing either $C_{(x)}$ or $C_{(v)}$ on the ordinate versus $C_{(t)}$ on the abscissa produces a standard QQ plot. Patterns in the QQ plot can be used to analyze structure in the spectral data, and the significance of the correlation between $C_{(t)}$ and $C_{(x)}$ can be used as an indication of the existence of subclusters in the spectral data. In the plot, a straight line with unit slope and an intercept of 0 indicates that the two CDFs are essentially identical (this line should be observed when $C_{(v)}$ is on the ordinate and $C_{(t)}$ is on the abscissa). The presence of breaks in the line indicates that the CDF on the ordinate is multimodal (i.e., that the test set and training set of samples are not the same). Sharp bends in the QQ line also indicate the present of more than one distribution in the CDF on the ordinate.

The Pearson Product Moment Correlation Coefficient between the two integrals or CDFs is used as a means of quantifying the differences between the test set and training set. The correlation between the two integrals decreases steadily with time when an IV bag is contaminated. The correlation coefficient can be used to provide both an indication of the number of microorganisms present in a sealed container as well as how long the microorganisms have been present in the container and what kind of microorganisms are present in the container. The identification of microorganisms is accomplished by preparing training sets of each type of microorganism expected in the bag and projecting test spectra into a training set space or library. Overlap should occur between the test group and one of the groups in the training set library if the test bags are contaminated with one of the microorganisms used to develop the training set library.

Microorganism Growth. Each bag contained approximately 0.1 mg/mL phenol because this preservative is present in the drug formulation of Zantac Injection. Although this phenol level is insufficient to preserve the bags, it is high enough to decrease organism growth rates. The slightly elevated ambient temperature of the laboratory (30°-35° C.) needed to facilitate operation of the near-IR spectrometer also had an effect on microorganism growth. The high ambient temperature increased the growth rate of *Pseudomonas aeruginosa* but decreased the growth rates of *Aspergillus niger* and *Candida albicans*. These results were determined by storing two duplicate bags for each microorganism at 20°-25° C. and determining their growth-rate profile over 48 hours in a similar manner. In all cases, solutions remained clear throughout the course of the experiment with no visible signs of product contamination.

Near-IR Results. The baselines and peak heights of repetitive scans differ somewhat because each spectrum was taken at a different location on the Viaflex bag. Accordingly, the thickness of the plastic and aqueous sample sampled can vary somewhat with each scan. Moreover, it is apparent from looking at the near-IR spectra of water and the PVC plastic from the bag that there are only a few relatively narrow spectral regions that may have high sensitivity for looking at back-reflected or scattered light from cells inside vials or bags. The regions around 1450 nm, 1940 nm, and 2500 nm are effectively obscured by intense water absorption. The PVC plastic strongly absorbs around 1729 nm. Therefore, measurements of Near-IR light returning through the water and the bag into the detector in the fiber optic probe should be best in the 1100-1360 nm region, in a small region around 1600 nm, and in the 2000-2400 nm region. Unfortunately, the background absorption in the 2000-2400 nm region from water is still quite high, so this region is virtually useless unless all of the material one wishes to examine is adhered to the bag wall, which minimizes the amount of water that the signal must pass through. The fact that water absorbs more strongly in the "windows" around 1600 nm and 2200 nm than in the window from 1100-1360 nm means that one should be able to determine the location of microorganisms (a type of depth profiling) by looking at spectral absorbances at 1100, 1600, and 2200 nm. For example, light scattering from free-floating microorganisms should appear mainly at the 1100-1360 nm region. However, microorganisms adhering to the walls of the container should appear at the 1600 and 2200 nm regions as well as in the 1100-1360 nm region. In fact, one might expect them to appear more strongly in the 1600 and 2200 nm regions than the 1100-1360 region because their absorption coefficients should be higher at the higher near-IR wavelengths than at the lower near-IR wavelengths. Therefore, because the pathlength for material adhered to the wall would be very limited, signals for microorganisms adhering to the walls would be expected to be more intense in the 1600 and 2200 nm wavelength regions. Spatial profiling can also be accomplished with the near-IR method. A three-dimensional picture of the contents of the bag can be roughly obtained if the bag is held motionless and multiple scans are obtained by moving the fiber-optic probe.

Figure 7:
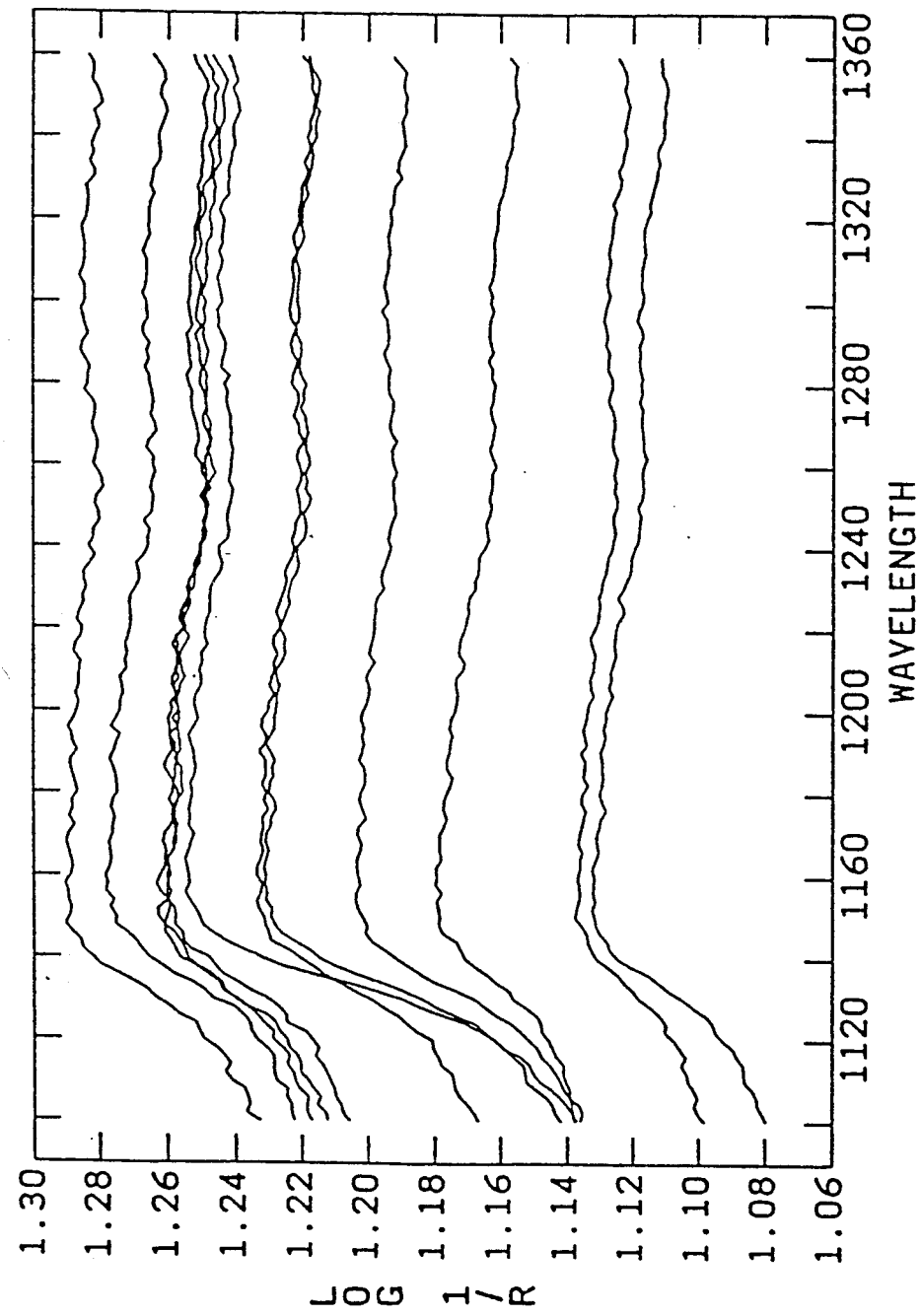
FIGS. 7 and 8 depict the spectra for PVC IV bags containing 5% dextrose and 0.5% aqueous dextrose without and with digital filtering, respectively.

In a preliminary study, full spectral scans from 1100-2200 nm were obtained for two inoculated bags. No significant absorbances were observed in the 1600 and 2200 nm regions, and it was believed that microorganisms injected into the bags were floating freely in solution. This study was therefore confined to the 1100-1360 nm region. FIG. 7 shows 12 spectra taken from a single bag. These spectra are raw spectra and are not processed by any filtering methods. They cover the entire spectral range from 1100-1360 nm. The spectra appear to be relatively noisy because very little light is actually reflected back into the probe from the sample. During the first few hours of cell incubation, few cells are in the solution and very little contamination exists.

Figure 8:
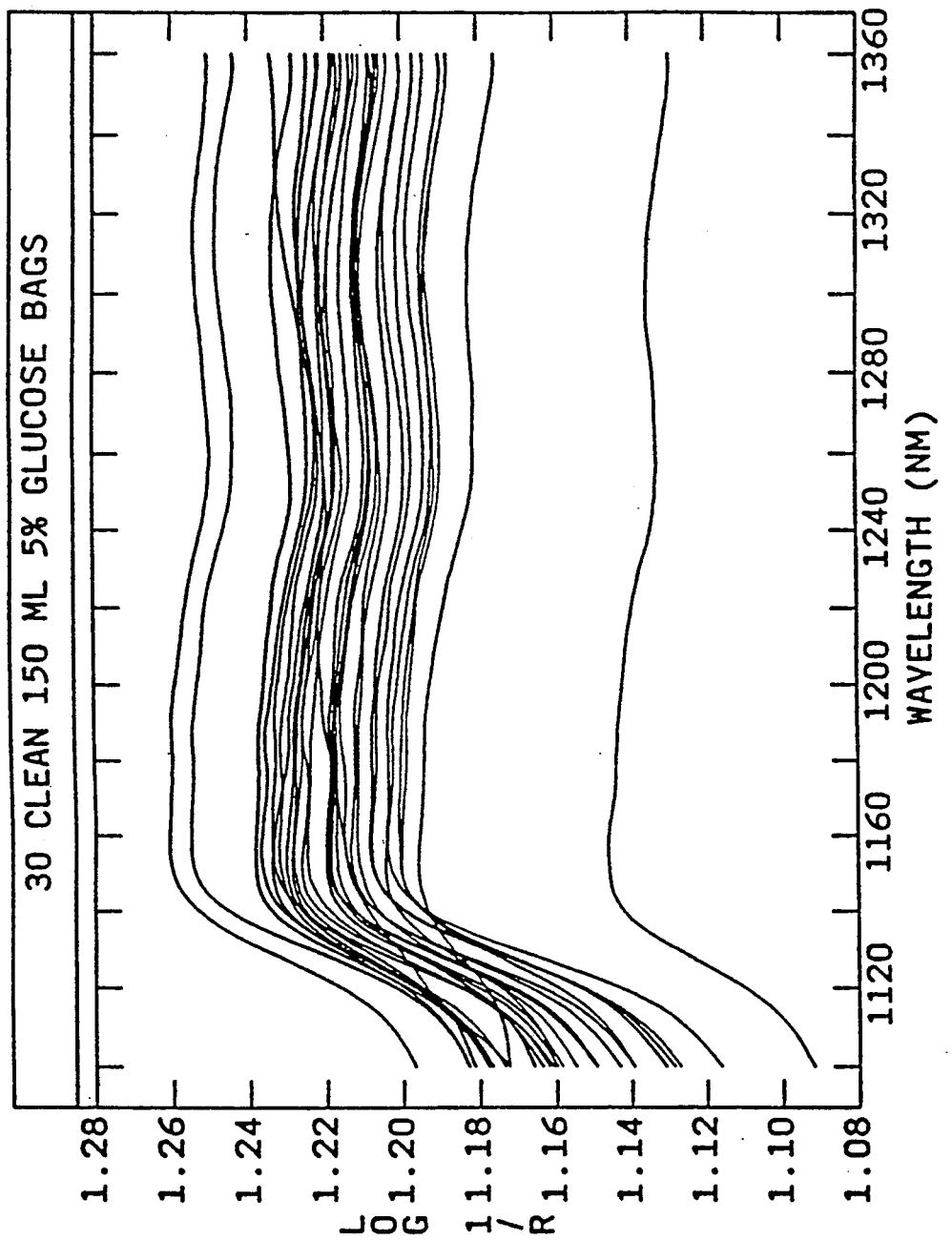

Spectra are filtered digitally and the 12 spectra taken from a single bag are processed to combine them into a single spectrum. The process of digitally filtering the spectra produces smooth and relatively noise-free curves such as those shown in FIG. 8. The data in FIG. 8 come from 30 clean (i.e., uncontaminated), 150 mL, 5% dextrose bags containing drug. At the early stages of contamination, it is important to move the probe around the bag because light will be scattered and reflected back to the probe only in a few locations where cells are present. The observation of scattering during the first few hours of incubation appears to be somewhat of a statistical phenomenon.

The mathematical problem is first one of identifying which of the 12 spectral scans from a bag actually show back-scattered light. Identifying and quantifying the cells is then accomplished using these particular scans. The first derivative is calculated for each of the 12 spectra and the absolute value of the first derivative in the regions near 1100 nm and 1260 nm were examined more closely. The sum of the absolute values of the first derivatives in these two regions was calculated for each of the 12 spectra, and the spectra showing the maximum sum were used to create a new spectrum. If the same spectrum has the maximum absolute value of the first derivative at both wavelengths, then it is the only spectrum selected, and the resulting, noralized curve is symmetrical around the zero wavelength displacement point.

Figure 9:
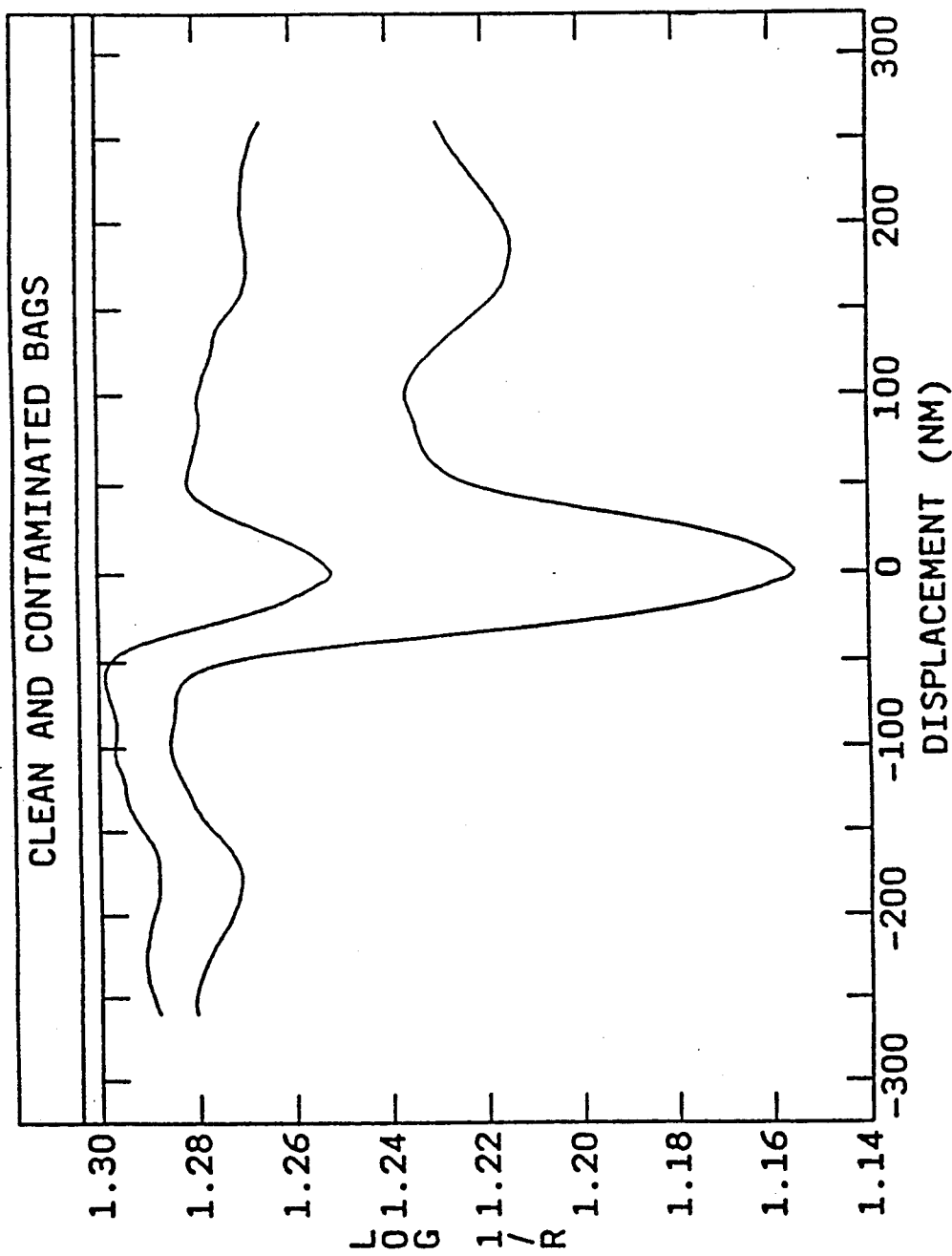
FIG. 9 depicts near-IR spectra of IV bags containing 5% dextrose and 0.5 mg/mL ranitidine after mathematical preprocessing as described herein with the upper trace being for a sterile bag and the bottom trace being for the bag contaminated with bacteria.

FIGS. 1 and 2 demonstrate why this spectra preprocessing was necessary. FIG. 1 shows 12 scans taken from an uncontaminated bag. The solid line shows the curve with the maximum absolute value of the first derivative. FIG. 2 shows 12 scans taken from a contaminated bag containing bacteria. The solid line again shows the spectrum with the maximum absolute value of the first derivative. It is evident that in clean bags, the major source of spectral variation is a baseline variation that is predominantly pathlength-dependent. In contaminated bags, however, certain spectra will show large back scattering peaks that appear as dips in the spectra near 1100 nm and 1260 nm. Other scans on the contaminated bag will show no back scattering at all. The value of the preprocessing technique for IV-bag spectra becomes apparent when one examines FIG. 9, which shows scans for both uncontaminated and contaminated IV bags. In FIG. 9, the displacement value of zero represents the back scattering observed at 1100 nm. The displacements that appear at 160 nm (both positive and negative) represent scattered light observed at 1260 nm in the original spectra. In FIG. 9, the lower curve is obtained from a contaminated bag while the upper curve is obtained from a clean uncontaminated bag. The preprocessing and filtering procedure is used to select the spectra that show the most back scattering of light, and these spectra are transformed to principal axes and used in the hyperspace integrating method. Integration of spectral clusters in hyperspace begins with forming an estimate of the population distribution in hyperspace from the existing training and test sets. This estimate is formed by a bootstrap process.

The training set, test set, and validation set each have a CDF. The CDFs for the training set, test set, and validation set are given by Equations 10, 11, and 12, respectively. Plotting the elements of the vector for the training set on the abscissa versus the elements either of the test set or of the validation set on the ordinate produces a standard QQ plot. When two CDFs match, the result of the QQ plot is a straight line with a slope of 1 and an intercept of 0. However, if the two CDFs are different, bends or breaks appear in the line of the QQ plot. The presence of bends (where two lines appear in the QQ plot with different slopes) indicates the presence of two groups in hyperspace with different sizes. The presence of a break in the QQ plot line indicates two groups in space centered at different locations. The presence of both a bend and a break indicates that two groups have different sizes and locations in multidimensional hyperspace. Applying linear regressions to the points on the QQ plot produces an equation whose linear coefficients have particular significance. When the spatial volume of the test set is smaller than that of the training set, the slope and intercept of the linear equation, determined by regression, have values between 0 and 1. However, when the volume of the test set is larger than that of the training set, the coefficients of the straight line through the QQ plot tend to have a large positive slope and a large negative intercept. Confidence limits are set on the correlation between the two CDFs in the QQ plot. The confidence limits are set through a bootstrap process similar to that used in equations 1-5.

Figure 10:
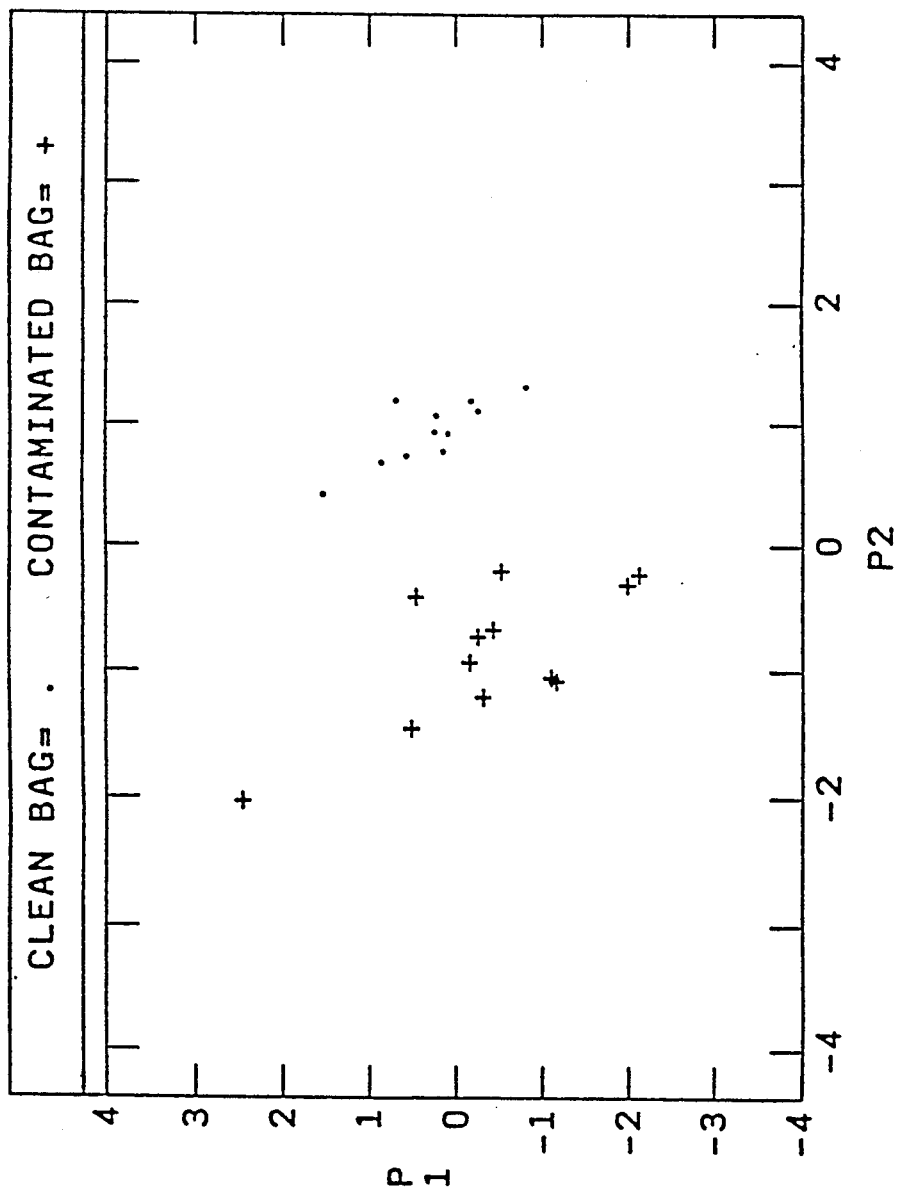
FIG. 10 depicts 12 spectra from a bag contaminated with bacteria compared to 11 spectra acquired from an uncontaminated bag.

FIG. 10 depicts the projection of spectra of a clean bag (given by points) and a contaminated bag (given by pluses) on a plane in multidimensional hyperspace. The plane corresponds to that defined by the first and second principal axes. FIG. 10 demonstrates that contaminated bags produce spectral points in hyperspace that are more widely scattered than clean bags. The larger spectral cluster of the contaminated bag occurs presumably because its spectra are more variable. The spectra in FIG. 10 represent 12 scans taken at various locations on each of the two bags (one clean bag spectrum with an A/D spike was eliminated). The fact that the pulses from the contaminated bag do not overlap the cluster formed by the points from the clean bag indicates that a spectral difference exists between the clean bag and the dirty bag. The distance between the cluster of points formed from spectra of the clean bag and the cluster formed from the contaminated bag provides an indication of the amount of material that is responsible for the contamination of the dirty bag. The direction of the displacement from the center of the clean bag provides an identifying spectrum of the material responsible for the contamination. Thus, distance gives an indication of the number of microorganisms that are present in the bag, while direction identifies the microorganisms present in the bag that are responsible for the contamination.

Figure 5:
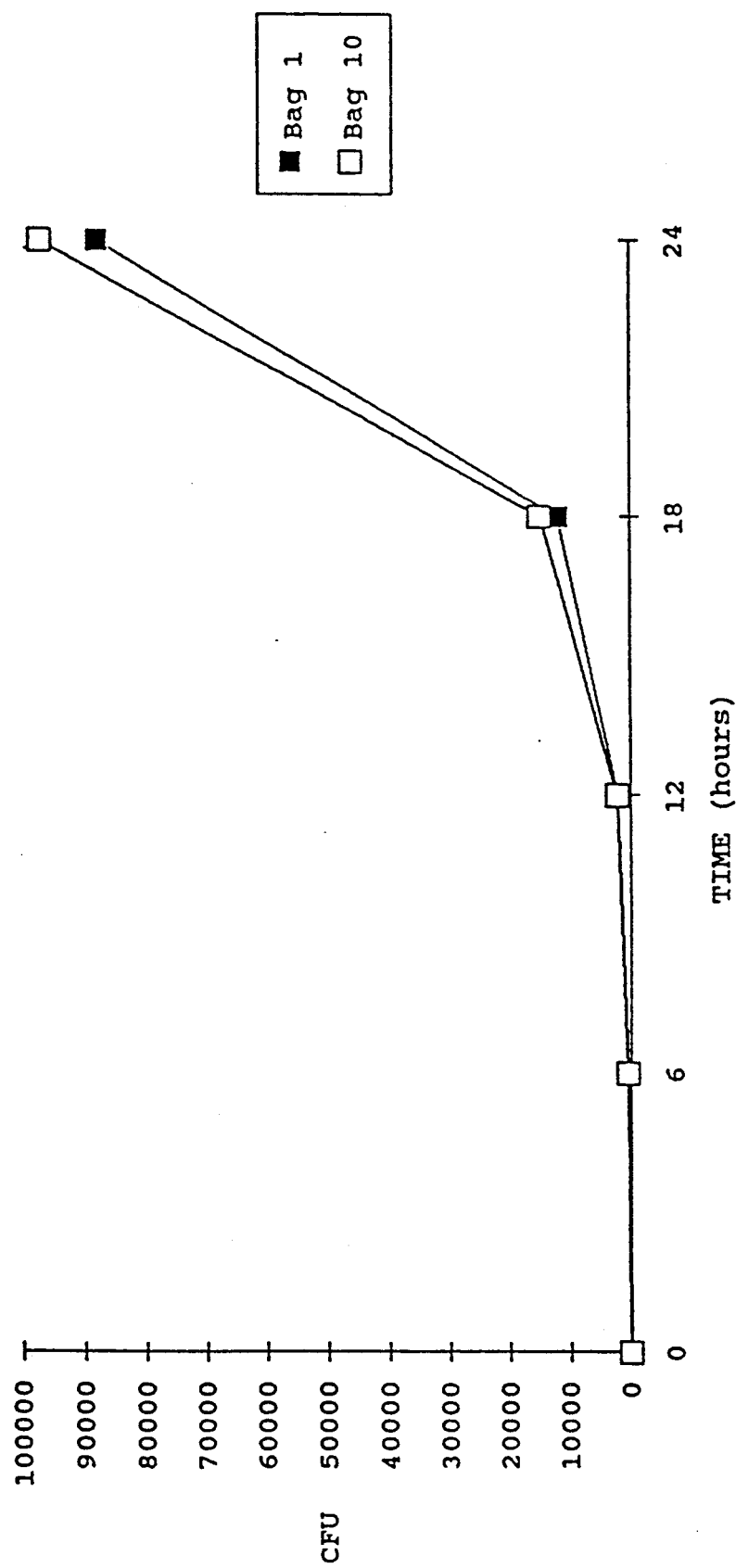
Figure 6:
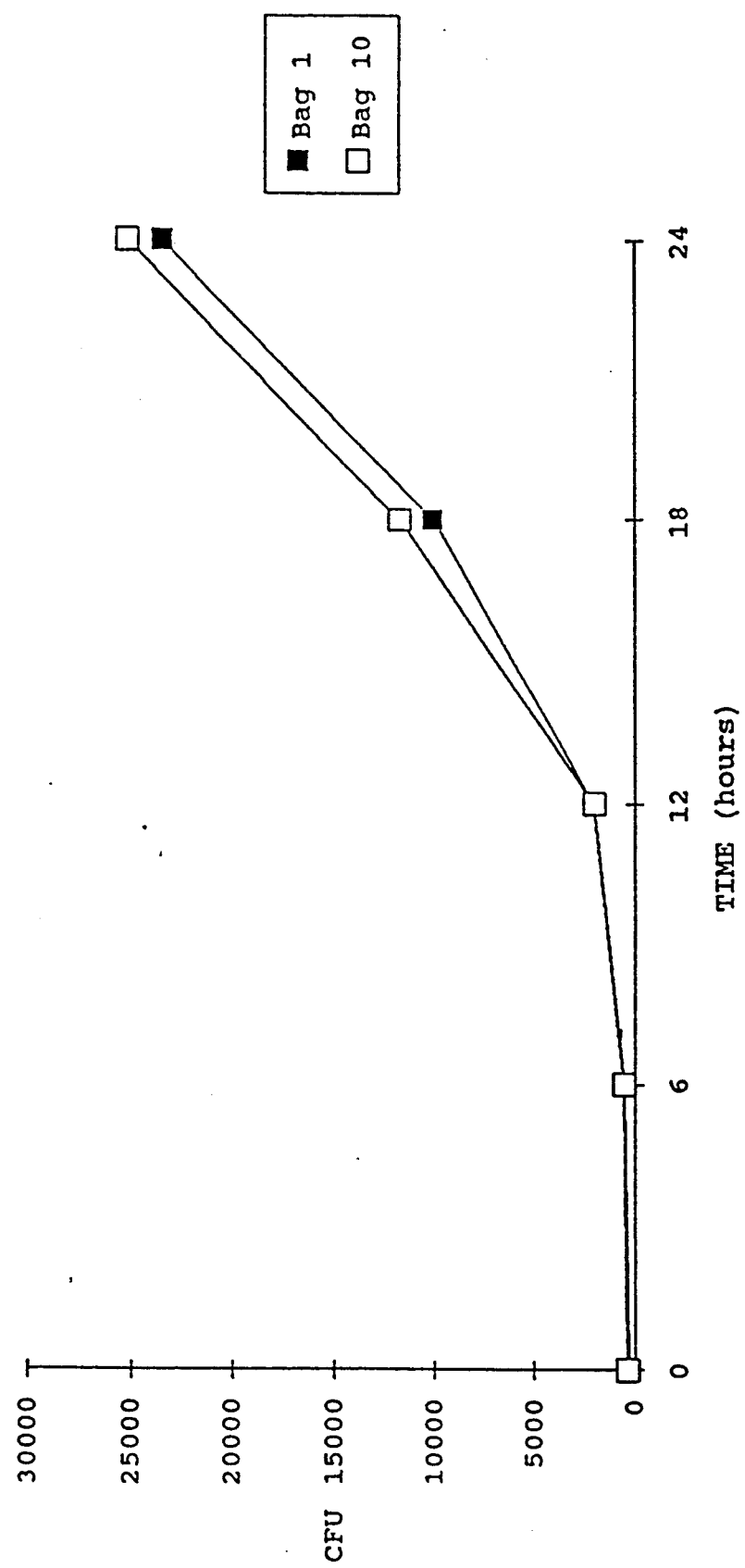
Figure 11:
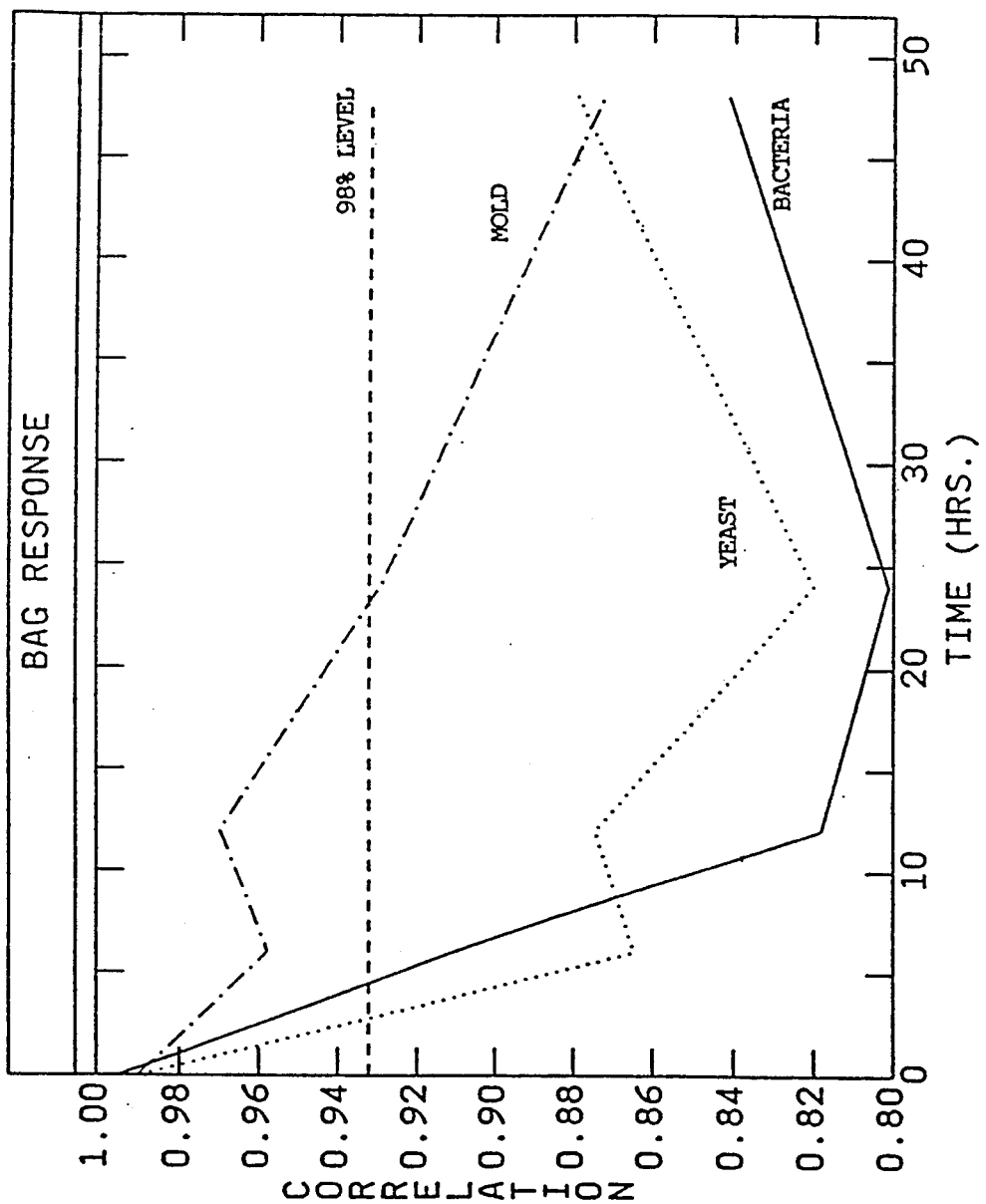
FIG. 11 depicts the change in correlation of test bags as mold, yeast and bacteria grow in the bag compared to their respective values immediately after inoculation.

FIG. 5 gives the growth curve for the yeast, *Candida albicans*. The assay for *Candida albicans* was obtained through standard microbiological assay. The same technique was employed to determine the concentrations of the bacteria, *Pseudomonas aeruginosa*, and the mold, *Aspergillus niger*, that appear in FIGS. 4 and 6, respectively. FIG. 11 is calculated from scans that have been averaged for each of the 10 bags having the concentration shown in FIGS. 4, 5 and 6. FIG. 11 is, in effect, a "growth curve" of sorts measured by back scattering of near-IR light from the bags and/or retroreflector. The 98% confidence limit on back scattering from clean training set is given as the horizontal short-dashed line in FIG. 11 (the level slightly above 0.93). The solid line represents the bacteria, the dotted line represents the yeast, and the dashed-dotted line represents the mold. After inoculation with 165 cfu per IV bag, the bacteria (*Pseudomonas aeruginosa*) were observed at about six hours at an average concentration of $57\pm4$ cfu/mL per bag. After injection of 10 cfu yeast (*Candida albicans*) per bag, growth was detected at about four hours with less than an average concentration of $3\pm1$ cfu/mL per bag. Injection of the mold (*Aspergillus niger*) at a level of 12 cfu per bag allowed detection of growth by near-IR spectrometry at about 24 hours at an average concentration of $145\pm20$ cfu/mL per bag.

In FIG. 11, it appears that the yeast is the fastest growing species in the bags. More specifically, about four hours after inoculation, the yeast bag is seen to begin to lose correlation to its initial values indicating a lack of sterility. For bacteria, this threshold appears to be about six hours, whereas for mold, this threshold occurs at about 24 hours. The 98% line indicates the correlation level at which bags can be considered to be significantly different (statistically); two uncontaminated bags will appear above this line 98 times out of 100.

In considering this data, it should be appreciated that yeast cells range in size from 3-14 $\mu$m and are larger than bacterial cells (about 0.5-2 $\mu$m). At least initially, this size advantage might make yeast a better source of light-scattering material than the bacteria, which actually grows faster. Eventually the bacterial growth appears to overtake the size advantage of yeast, and the bacteria then give the strongest back-scattering signal. Mold is intermediate in size (approximately 3-8 $\mu$m) and the slowest growing species as indicated by its continued correlation change up to nearly 50 hours, while the correlation of the yeast and bacteria seem to have begun to level off, presumably because of the preservative (phenol) also present in the drug. What is most noticeable in FIG. 11, however, is that even at six hours and below, the near-IR method is able to detect contamination at a 98% confidence limit for yeast and bacteria. FIGS. 4 and 5 indicate that neither the yeast nor the bacteria have grown significantly after this short period of time. Nevertheless, the near-IR method is still able to detect this contamination. The correlation between spectral clusters at six hours is poor for *Candida albicans*, *Pseudomonas aeruginosa*, and *Aspergillus niger*. The poor correlation between the spectral clusters at all times (at six hours and beyond) suggests that the near-IR method is able to differentiate between these cell types as well as possible to provide an indication of the extent of their growth.

Summary of Results. These data suggest that changes in near-IR spectra, taken through the IV bags with a fiber optic probe and without product tampering, correlate to organism growth. Moreover, spectra also distinguish between bags contaminated with different classes of microorganisms. Integration of the method of the invention with mechanical techniques in product processing will allow an on-line sterility assurance method in parenteral-production facilities, particularly for filling processes e.g., aseptic-fill that require very careful control and monitoring because of less than desirable assurance levels. The inability in the prior art to test all parenteral units in an automated fashion is a serious limitation to conventional microbiologic testing, particularly in cases where microbial contamination is not distributed uniformly throughout a batch (Henry L. Avallone, *J. Parenter. Sci. Technol.*, 1985, 39(2), 75–79 and Henry L. Avallone, *J. Parenter. Sci. Technol.*, 1986, 40(2), 56–57). It is very difficult, if not impossible, to detect a small percentage of contaminated units within a large batch. Near-IR spectrometry with a fiber-optic probe according to the present invention can be used as an alternative or adjunct method to conventional microbiologic testing in quality assurance and other applications where large quantities of cells must be identified and quantified in a relatively short period of time.

The variation in replicate spectra taken from the same IV bag is larger than that observed with other containers because of the flexibility of the PVC and poor near-IR transparency. To reduce the number of replicate scans needed and to improve confidence statistics, further optimization and improvements can be carried out in the sampling procedure, e.g., configuration of the optical probe, sample container and wavelength range scanned.

In accordance with a further aspect of the present invention, an alternative mathematical technique is used in conjunction with near-IR spectroanalysis to successfully detect contamination of a product through intact vials including those formed from glass. Once again, the evaluation may be advantageously completed noninvasively and nondestructively without sample preparation. Accordingly, the product is not destroyed. Additionally, no contamination may possibly be introduced into the product by the testing method. Hence, the tested product may subsequently be used.

More specifically, the alternative mathematical technique corrects for both background and sample-matrix interferences utilizing a computerized modeling process that is applied to the near-IR signals. Further, the technique may not only be used to detect the contaminants *Candida albicans, Aspergillus niger* and *Pseudomonas aeruginosa* but also other bacteria including, for example, *Staphylococcus aureus, Pseudomonas cepacia* and *Escherichia coli.*

In accordance with this alternative approach, the detection of cells in drug solutions is also based on the ability of a spectrometer and a computer to identify small changes in groups of spectra obtained from a single unit of a product. To identify these changes successfully, spectra recorded at d wavelengths are projected as single points in a d-dimensional hyperspace. Spectral points obtained from sterile vials tend to cluster in a small region of hyperspace. These points are designated the training set T (see FIG. 12). When vials become contaminated, the spectra of the contaminants cause a displacement in the position of the spectral cluster X (obtained from contaminated vials) in hyperspace. In addition, spectra obtained from the same vial tend to be less reproducible when the vial is contaminated, leading to an increase in the volume of the spectral cluster in hyperspace. Simultaneous changes in position and volume of spectral clusters can be determined by comparing two integrals:

1. the integral of the training set T, from the center of T to the surface of T, and
2. the integral of T, from the center to the surface, after T is augmented by X.

In actuality, T and X are never precisely known, but rather are represented by a discrete estimate of spectral points obtained from representative vial samples. In order to increase the reliability of these estimates, all spectra collected are filtered similarly to reduce the effects of noise on the integral analysis.

The spectral filter is a function designated S that is used to represent near-IR spectra in the form of smooth cubit splines that pass near, but not through, the actual spectral data values:

$$T = S(W_1, Y, W, t_L, \delta) \qquad eq\ 28$$

or $$X = S(W_1, Y, W, t_L, \delta) \qquad eq\ 29$$

S fits smooth curves constructed of cubic splines to the spectra Y(W). $W_1$ specifies the independent variable values (wavelengths) to which interpolation is made. Y is made up of the dependent variable values (absorbances or logarithms of reciprocal reflectances) that are to be interpolated. W contains the independent variable (wavelength) values corresponding to Y, and is generally (though not necessarily) the same as $W_1$. The scalar $t_L$ is a tolerance value that controls the extent of smoothing, and is the acceptable root mean square relative deviation of the fitted curve:

$$RMS(Z) \leq t_L, \text{ where } z_j = F(w_j - y_j)/\delta_j. \qquad eq\ 30$$

$\delta$ is an array of the estimated errors (is SDs) in the absorbance values Y. The smoothing splines are of the form:

$$F(W) = A_j\Delta + B_j\Delta + C_j\Delta 2 + D_j\Delta 3 \qquad eq\ 31$$

where $w_j \leq w \leq w_{j+1} [1 \leq j \leq m-1]$, $\Delta = w - w_j$, and m is the number of wavelengths in the W and Y arrays. Note that $W_1$ may have a different number of wavelengths (columns) than W and Y. The resulting filtered spectral set (either T or X or both) has as many columns as $W_1$, and as many rows as the number of spectra to be smoothed (i.e. the number of rows of Y).

The BEST is a flexible clustering procedure that is applied to the smoothed spectra. Extending the method to search for subclusters within a training set requires a filtered training set T and test set X, as well as the calculation of these sets' respective bootstrap distributions, B and $B_{(X)}$. The discussion that follows outlines one route to a solution to the subcluster-detection problem.

A training set of sample spectral values (e.g., reflectance or absorbance), recorded at d wavelengths from n uncontaminated vials, is represented by the n-by-d matrix T. (Often, another n-by-d matrix V, containing validation vials, is also assembled from uncontaminated vials like the training set. The sample set V serves as an indicator of how well the training set T describes the overall population variation of spectral values obtained from uncontaminated vials.)

The second step of the basic BEST calls for the calculation of bootstrap distributions. Bootstrap distributions can be calculated by an operation $\kappa$; $\kappa(T)$, $\kappa(X)$, and $\kappa(V)$ are each calculated in this manner. The results of the $\kappa$ function are the m-by-d arrays B, $B_{(X)}$, and $B_{(V)}$.

The operation $\kappa(\tau)$ begins by filling a matrix P with sample numbers to be used in bootstrap sample sets $B_{(s)}$:

$$P = p_{ij} = \tau. \qquad eq\ 32$$

The values in P are scaled to the training-set size by:

$$P = [(n-1)P + 1] \qquad eq\ 33$$

A bootstrap sample is then created for each row i of the m-by-d bootstrap distribution B by $$B_{(s)} = t_{kj} \qquad eq\ 34$$

where $\kappa$ are the elements of the i-th rows of P. The q-th row of B is filled by the center of the q-th bootstrap sample $$b_{qj} = \sum_{i=1}^{n} b_{(s)ij}/n \qquad eq\ 35$$

and the center of the bootstrap distribution is $$c_j = \sum_{i=1}^{m} b_{ij}/m \qquad eq\ 36$$

The operation $\kappa$ is then repeated using the vial spectra in X and V.

The multivariate data in the bootstrap distributions are then reduced to a univariate form:

$$s_{(T)i} = \left( \sum_{j=1}^{d} (b_{ij} - c_j)^2 \right)^{\frac{1}{2}} \qquad eq\ 37$$

$$s_{(X)i} = \left( \sum_{j=1}^{d} (b_{(X)ij} - c_j)^2 \right)^{\frac{1}{2}} \qquad eq\ 38$$

$$s_{(V)i} = \left( \sum_{j=1}^{d} (b_{(V)ij} - c_j)^2 \right)^{\frac{1}{2}} \qquad eq\ 39$$

and these distances are ordered and trimmed according to a trimming-index set $$P_{(T)} = \{mp+1,\ mp+2,\ mp+3,\ \ldots,\ m-mp\} \qquad eq\ 40$$

to reduce the leverage effects of isolated selections at the extremes of the bootstrap distributions. A hypercylinder can be formed about the line connecting C to the center of $B_{(X)}$ or $B_{(V)}$, giving directional selectivity to the information in $S_{(T)}$, $S_{(X)}$, and $S_{(V)}$ if desired. $S_{(T)}$, $S_{(X)}$, and $S_{(V)}$ then have $n_h$ elements instead of m elements. Subclusters can be detected without this selectivity, however. While this directional selectivity adds to the sensitivity of the subcluster test, it also introduces a number of additional questions, e.g.: How small a radius is too small? How many replicates are required for a given radius? At what point is the additional sensitivity merely reacting to the particular training set selected, and not to any population characteristic? The validation of the spectrometric method for analysis of vials is complicated by the introduction of the hypercylinder, and the results of the method do not appear to be superior when the hypercylinder construct is applied to spectra obtained from the vials. Thus, the hypercylinder implementation of the BEST is not employed in the analysis of the vials.

Instead, cumulative distribution functions (CDFs) for quantile-quantile plotting are formed by:

$$C_{(t)} = \partial(S_{(T)}P_{(T)},\ S_{(T)}P_{(T)}) \qquad eq\ 41$$

$$C_{(X)} = \partial(S_{(T)}P_{(T)},\ S_{(X)}P_{(T)}) \qquad eq\ 42$$

$$C_{(V)} = \partial(S_{(T)}P_{(T)},\ S_{(X)}P_{(T)}) \qquad eq\ 43$$

Plotting the elements of $C_{(T)}$ on the abscissa versus the elements of either $C_{(X)}$ or $C_{(V)}$ on the ordinate produces a standard quantile-quantile (QQ) plot (2). Patterns in such a plot can be used to analyze structure in the spectral data obtained from the vials, and the significance of the correlation between $C_{(T)}$ and $C_{(X)}$ can be used as an indication of the existence of subclusters in the spectral data that reflect contamination in the vials. In the QQ plot, a straight line with unit slope and an intercept of 0 indicates that the two cumulative distribution functions are essentially identical (this should be observed when $C_{(V)}$ is on the ordinate, or when the test vial is uncontaminated). In the extended BEST QQ plot, the presence of breaks in the line indicates that the CDF on the ordinate is multimodal (i.e., that the test spectra and training spectra are not the same, and the test vial is contaminated). Sharp bends in the QQ line also indicate the presence of more than one distribution in the CDF on the ordinate, and indicate the presence of contamination.

Figure 12:
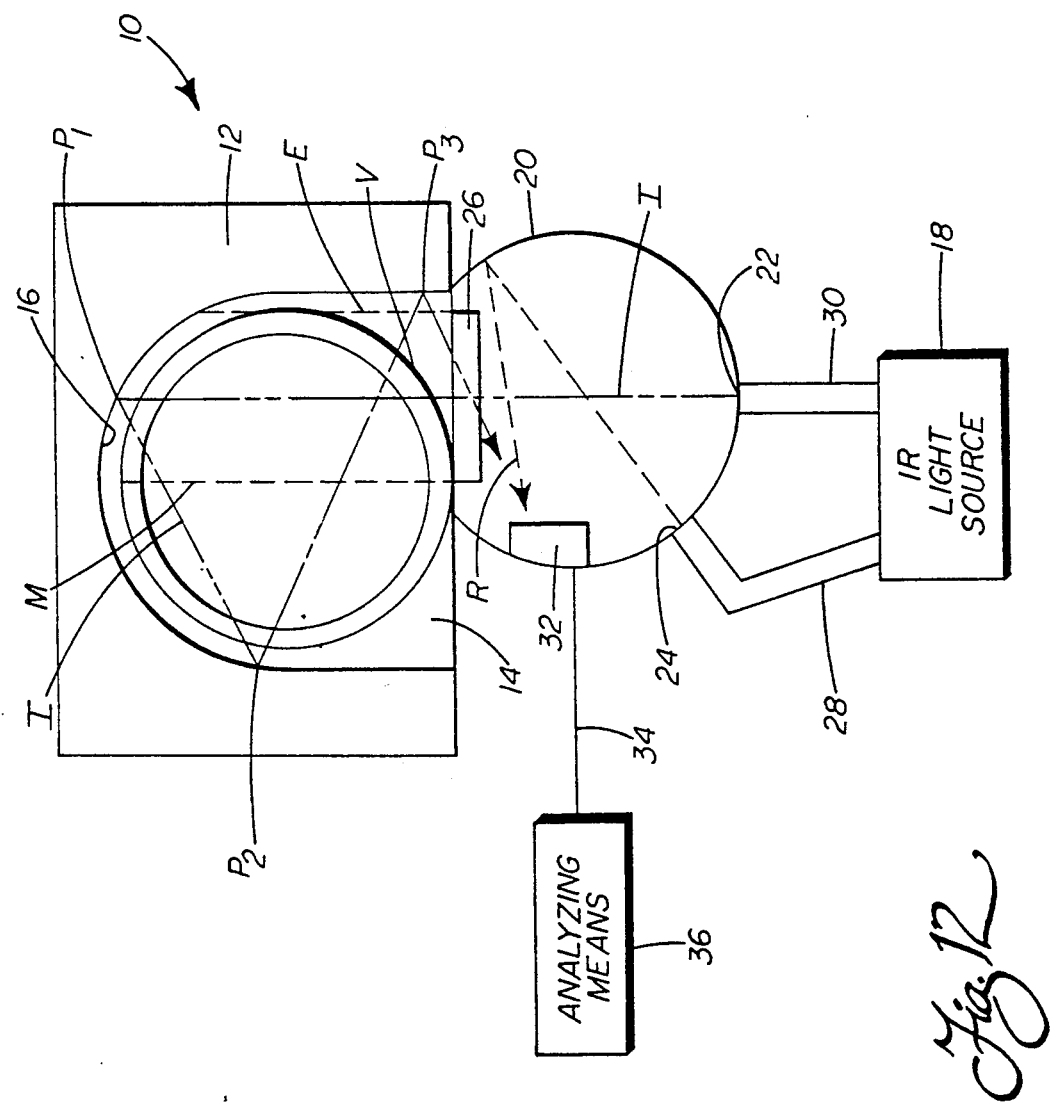
FIG. 12 schematically shows the apparatus of the present invention used to collect spectral data for conducting contamination analysis of products in vials.

The apparatus 10 of the present invention as shown in FIG. 12 includes a vial holder 12. The vial holder 12 may, for example, be formed of plastic and has a substantially U-shaped cavity 14. The cavity 14 has a width substantially corresponding to but just slightly larger than the diameter of the vial V to be tested. The U-shaped wall of the cavity 14 is lined with aluminum so as to provide a substantially U-shaped mirror 16.

The vial holder 12 advantageously serves to reduce stray light that would otherwise enter the apparatus 10 through the vial V and its contents. In certain situations this stray light could adversely effect contamination analysis by leading to false readings. Hence, this problem is significantly reduced. Additionally, as described in greater detail below, the U-shaped mirror 16 is also adapted to reflect the incident beam I several times through the vial V and the liquid product contained therein. Advantageously, this seems to significantly enhance the sensitivity of the apparatus 10 with respect to the detection of microorganisms.

The apparatus 10 also includes a near-infrared light source 18, such as in InfraAlyzer 500. The light source 18 is adapted to produce an incident beam I and a reference beam R of light having identical wavelength characteristics. The wavelength of light utilized to perform the analysis falls in a range of 800-2500 nm and, more preferably, 1100-1360 nm.

As shown, the apparatus 10 also includes an integrating sphere 20 such as a gold sphere having a one inch diameter. The integrating sphere 20 includes an incident beam port 22, a reference beam port 24 and a sample window 26 directly opposite the incident beam port. The reference beam R is carried from the light source 18 to the reference beam port 24 by means of a fiber optic bundle 28. Similarly, the incident beam I is carried from the light source 18 to the incident beam port 22 by means of a fiber optic bundle 30.

The reference beam R serves to compensate for noise caused by the bending of the fiber optic bundles 28, 30 and/or by source intensity variations. The reference beam R is directed through the port 24 so as to strike the inner reflective wall of the integrating sphere 20 and be reflected back toward a spectral detector 32. One such detector 32 that may be utilized for this purpose is an EDAPT-1 probe.

The incident beam I is directed from the port 22 through the sphere 20 and sample window 26 into the vial V and the liquid product contained therein. The incident beam I is then reflected by the mirror 16 at the point P, so as to pass again through the vial V and the product. Next, the incident beam I is again reflected by the mirror 16 at the point $P_2$ so as to pass for a third time through the vial V and the product. Finally, the incident beam I is reflected by the mirror 16 at the point $P_3$ back through the sample window 26 to the detector 32.

Any light of the incident beam I striking any solid contamination such as a microorganism; during the three passes through the vial V as described above is scattered, thereby changing the spectra. Scattered light reflected back through the sample window 26 is integrated/collected by the inner reflective wall of the sphere 20 and focused upon the detector 32. Changes in the spectra that could result from other causes such as incomplete transmission through the vial V or absorption by molecules in the solution are compensated for by comparing the actual spectra obtained to sample spectra of known standards or controls during subsequent analysis.

Signal values from the detector 32 are transmitted along a control line 34 to an analyzer 36. More specifically, the signal values are recorded as a ratio of intensities between the incident beam I and reference beam R. The logarithm of the reciprocal of the reflectance intensity is then used to complete the analysis by means of a computer such as described below in Example 2.

The first step is the placing of a vial V to be tested into the cavity 14 of the vial holder 12 so that the wall of the vial is adjacent the U-shaped mirror 16. A scanning plane is then selected and the integrating sphere 24 is positioned so as to align the sample window 26 with the selected scanning plane. When properly positioned along the open end of the mirror 16, the scanning window 26 extends lengthwise substantially between the median line M and outer edge E of the vial V adjacent the mirror (see FIG. 12). As shown by the incident beam line I in this drawing figure this positioning insures that the incident beam is directed through the vial V and its contents three times before being reflected back to the detector 32.

Any solid contaminants, such as microorganisms, present in the liquid product in the vial V in the scanning plane serve to scatter the light of the incident beam I. Portions of such scattered light pass back through the sample window 26 into the integrating sphere 20. The reflective wall of the integrating sphere serves to collect and focus the scattered light on the detector 32. Similarly, the reference beam R is reflected by the inner wall of the sphere 20 onto the detector 32. The detector 32 produces signals which are communicated along the control line 34 to a computer analyzer 36. Several other different scanning planes are also selected and spectral readings recorded. For example, up to ten or more scanning planes and readings may be recorded for a single vial. The resulting readings are then analyzed by the computer 36 and are also compared to known standards. This allows not only the existence of contamination to be determined but in many cases the extent and type of contamination as well.

EXAMPLE 2

Equipment. Near-IR energy was transmitted through the apparatus 10 described above using an InfraAlyzer 500 scanning spectrophotometer (Bran+Luebbe). Data was collected on an IBM PS/2 model 50 computer (IBM Corp., Armonk, N.Y.) running IDAS software (Bran+Leubbe). Collected reflectance values were then transferred to a MicroVAX II computer system (Digital Equipment Corp., Maynard, Mass.) and an IBM 3090-300E vector supercomputer. Spectral data was processed for analysis in accordance with the mathematical technique set forth in equations 28-43 using Speakeasy IV Epsilon and Zeta (Speakeasy Computing Corp., Chicago, Ill.) programs that were written specifically for this purpose (That is: BEST).

Materials. Thirty glass vials containing a nutrient medium were divided into 5 groups of six vials each. One group of six vials served as control vials, and were injected with nutrient medium. The vials in the other four groups were injected with a different species of bacteria for each group. The vials were injected through the rubber cap with a sterile disposable syringe and 21G×1.5 in. needle (Becton Dickinson, Rutherford, N.J.).

The microorganisms injected were: *Staphylococcus aureus* (American Culture Collection number (ATCC no. 6538), *Pseudomonas cepacia* ATCC no. 25416), *Escherichia coli* (ATCC no. 8677), and *Pseudomonas aeruginosa* (ATCC no. 9027). These microorganisms were chosen to include a spectrum of bacteria that must be monitored to meet USP and FDA requirements.

Inoculum was prepared by transferring the respective microorganisms from a lyophilized culture onto a solid agar medium and incubating at suitable temperatures for sufficient growth. For *Pseudomonas aeruginosa*, Trypicase Soy Agar was used, and the incubation time was 18-24 hours. The agar and incubation time is consistent with harvesting procedures for pharmaceutical microbiological assays.

Cell concentrations were adjusted to a target range of 10-100 colony-forming units (cfu) per 0.10 mL using Trypicase Soy Broth. This range was selected to give a starting target concentration of less than 1 cfu per bag, which represents a reasonable contaminant load for a sterility violation. The number of cfu per mL in the inoculum was determined in quadruplicate by the spread-plate method. The averages from four plates were 12.0 cfu/mL, 120.0 cfu/mL, 444.0 cfu/mL, and 12.0 cfu/ml for *Staphylococcus aureus*, *Pseudomonas aeruginosa*, *Escherichia coli*, and *Pseudomonas cepacia*, respectively.

The cap of each of the 30 vials was injected with 0.10 mL of inoculum from one of the four microorganisms (6 vials of each type). The vials were inverted several times to distribute the cells throughout the vials.

Figure 13:
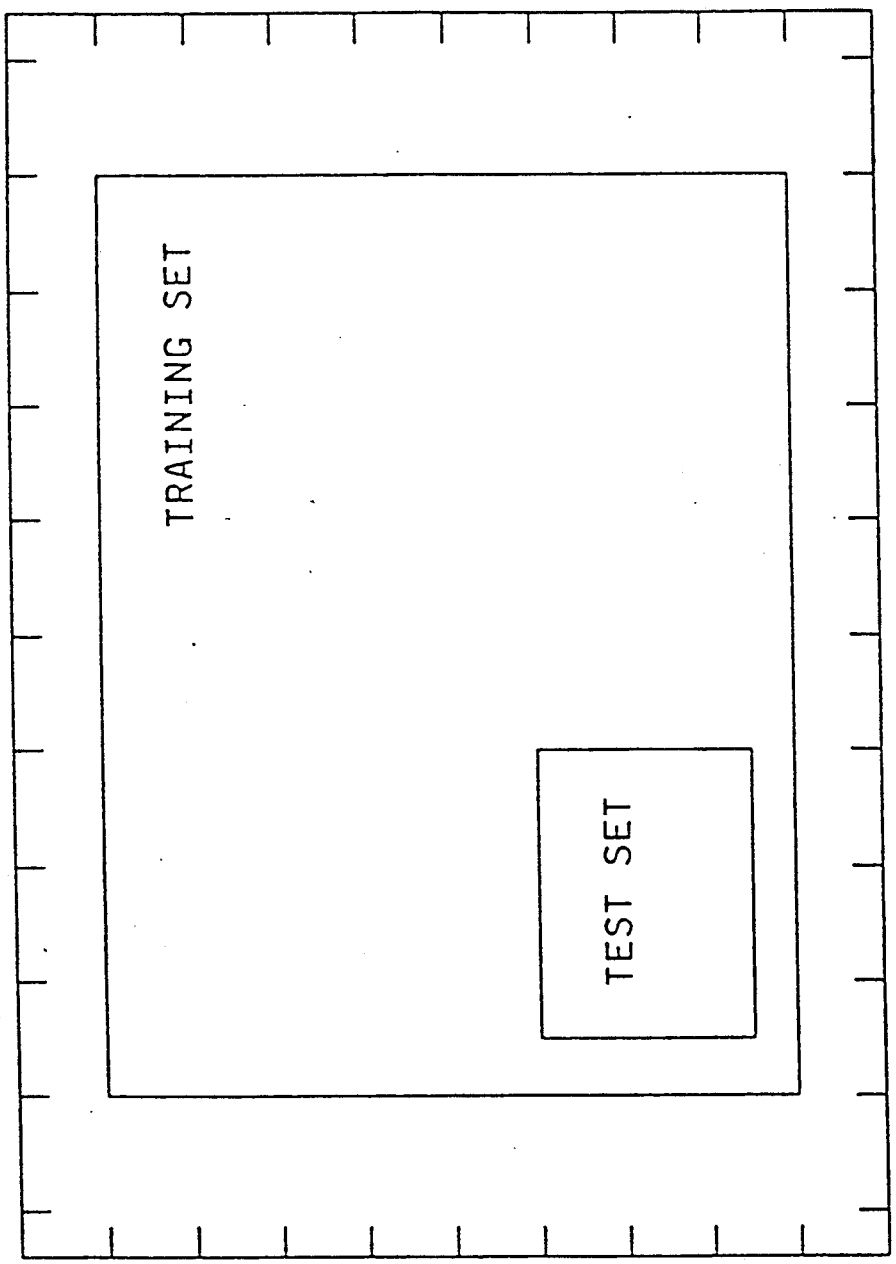
FIG. 13 is a schematic showing of the training set and test set projection process.
Figure 14:
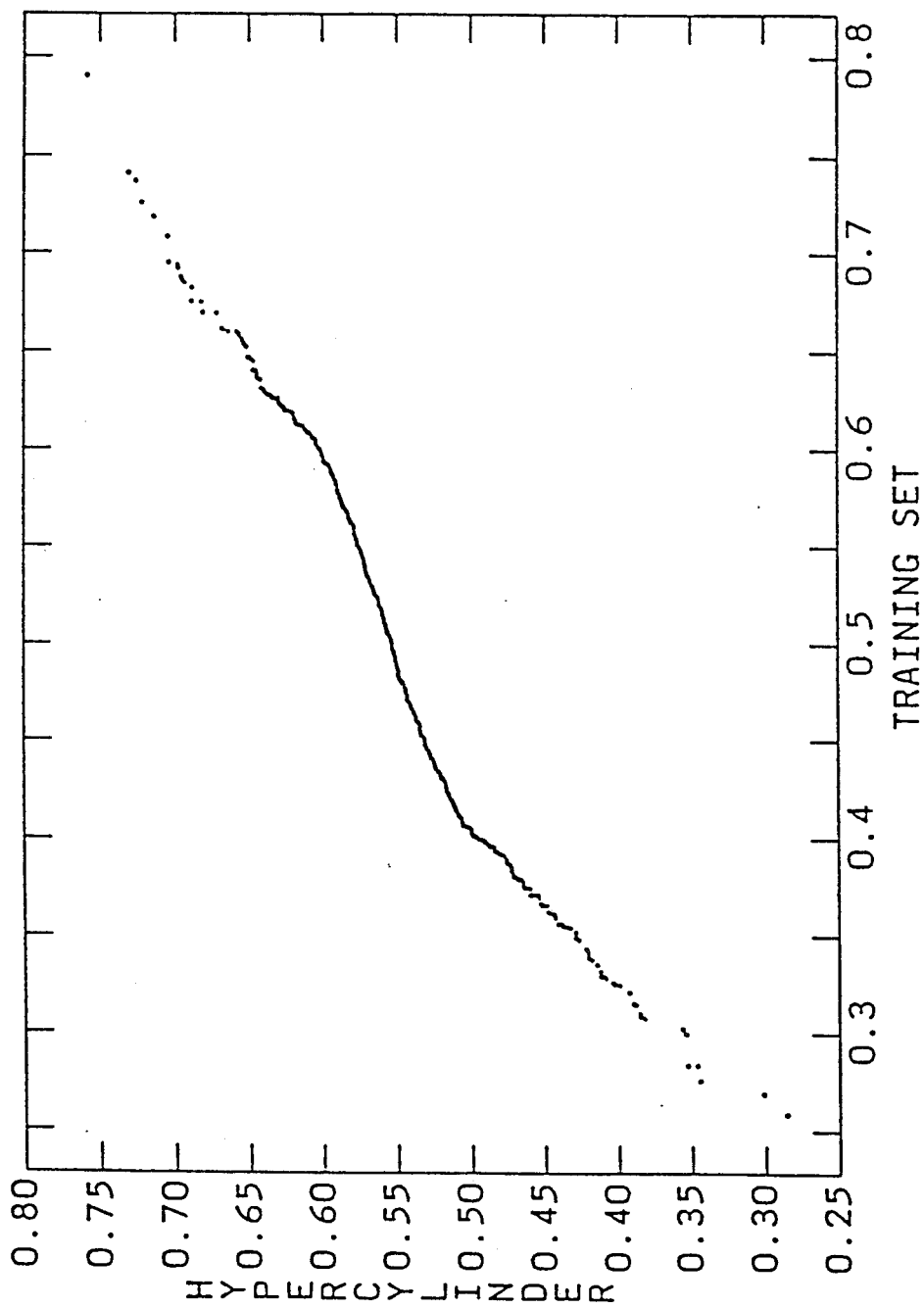
FIG. 14 is a quantile-quantile plot of two slightly different integrals, the result of the test set being slightly smaller than the training set.

Data Analysis. All six vials containing the same organism in each group were inoculated sequentially prior to collecting the training-set scans. The time lag between the scanning of the first vial and the sixth vial was approximately 30 minutes. Furthermore, 10 scans of the wavelength range from 1100-1360 nm were taken from each vial at slightly different positions on the vial. During spectral analysis, a spectrum recorded at 130 wavelengths in the 1100-1360 nm region was projected as a single point in a 130-dimensional-hyperspace. The analytical procedure located the center of the training set from the spectra recorded at time-zero in a 130-dimensional space and integrated outward steadily in all directions in space from the center of this training set to the "edges" of the training-set cluster (the edges are defined typically as being three multidimensional standard deviations away from the center). This integral forms a function that is compared to a second integral, which is determined by integrating from the center of the combined training set and test set of spectra (where the test set is the spectra of the vials at a later time, such as 6, 12 or 18, 24 or 48 hours after the injection of microorganisms). A plot of the first integral versus the second integral is used to form a QQ plot. FIG. 13 is a schematic diagram of the training set and test set projecting process. FIG. 14 is a QQ plot of two slightly different integrals that result from the projection of a test set into an augmented-set space when the test set is slightly different from the training set (here, the test set is slightly smaller in volume than the training set).

After scanning vials 1 through 6 from each group at 1, 6, 12 or 18, 24, and 48 hours, microorganism concentrations in vials 1 and 6 were measured by removing 0.40 mL of solution from each vial with a 0.5 mL sterile syringe. A 0.10-mL aliquot (or diluted aliquot at high concentrations) was transferred to each of four plates to determine the average cell concentration in cfu/mL. Trypticase Soy Agar was used as a growth medium for the Pseudomonas aeruginosa aliquots, and colonies were counted after 48 hours at 30°-35° C. The results for each microorganism (cfu/mL) are shown in the third column of Table 1.

Summary of Results. A total of 30 vials were prepared containing sterile nutrient media. Six of these vials were injected with additional sterile media and served as control vials over the 48 hours in which spectra were collected from all 30 vials. Six vials were injected with Staphylococcus aureus, six with Pseudomonas aeruginosa, six with Pseudomonas aeruginosa, and six with Escherichia coli. Each of the 30 vials were scanned 10 times immediately following injection, and these spectra are depicted in FIGS. 15-19 as the time=0 point. The vials were allowed to incubate at room temperature for two days. During this 2-day period 10 spectra were collected from each of the vials at 6, 12 or 18, 24, and 48 hours after injection. Integrals calculated from the center of a cluster of spectral points at time=0 were correlated to integrals calculated at a later time. The results of these correlations are presented in FIGS. 15-19. The solid line in each of these figures represents the average correlation of 6 replicate analyses of vials containing a certain type of injection (control injection or bacterial injection). The dashed lines represent ±1 error bars on the average correlation. The dot-dashed line signifies a 98% confidence limit on the time=0 spectra of a given injection type (i.e., 98% of the time, the correlation between 2 sets of spectra obtained from time=0 spectra of the given injection is higher than this value).

Figure 15:
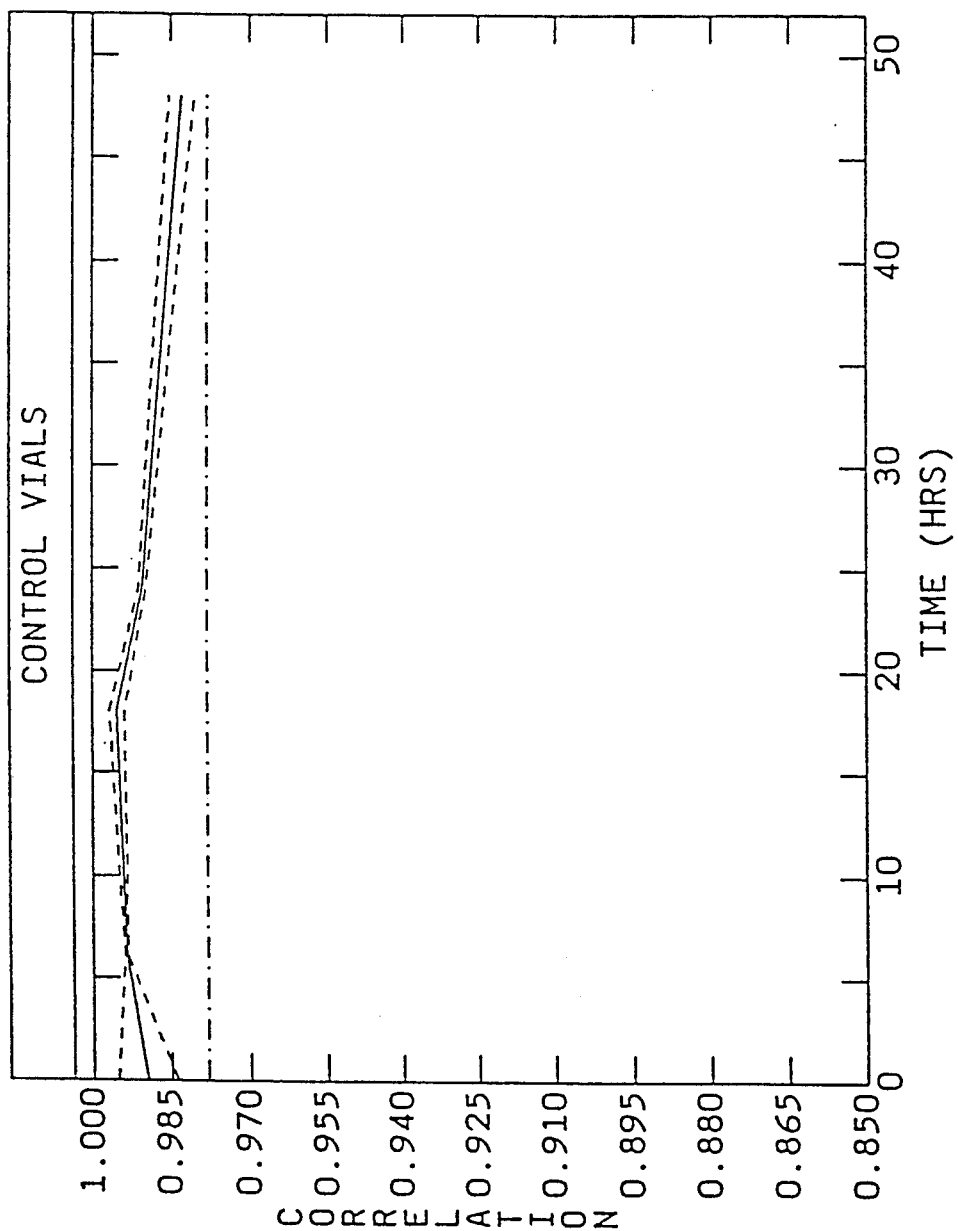
FIG. 15 is a spectra plot of control vials over time.

FIG. 15 depicts the change in spectra of the control vials with time. The spectra of the control vials do not change significantly (at the 98% level) over the 48-hour period.

Figure 16:
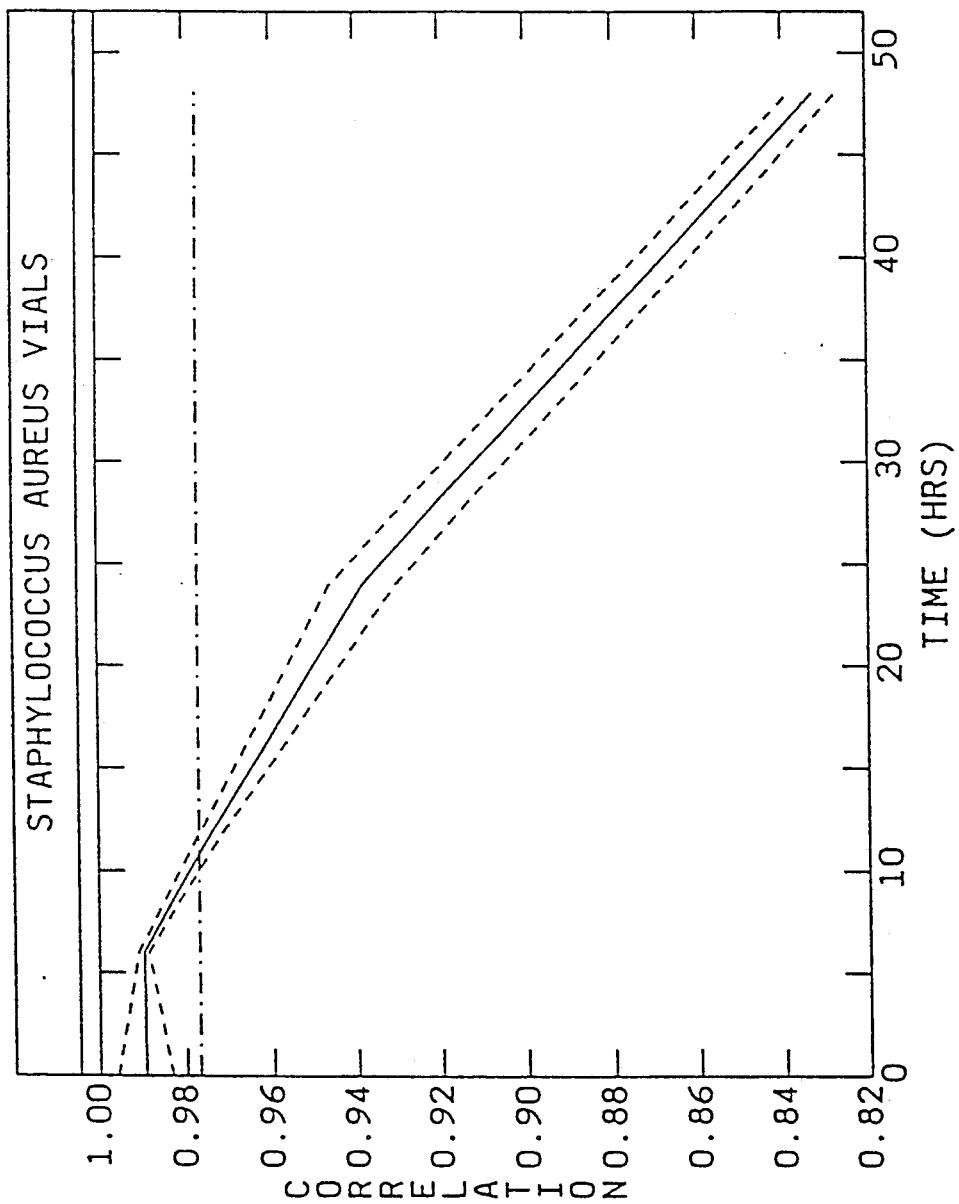
FIG. 16 is a spectra plot of *Staphylococcus aureus* vials over time.

FIG. 16 shows the change in the spectra of the vials injected with Staphylococcus aureus with time. The vials cross the 98% confidence limit between 11 and 12 hours after injection of 10-100 cfu.

Figure 17:
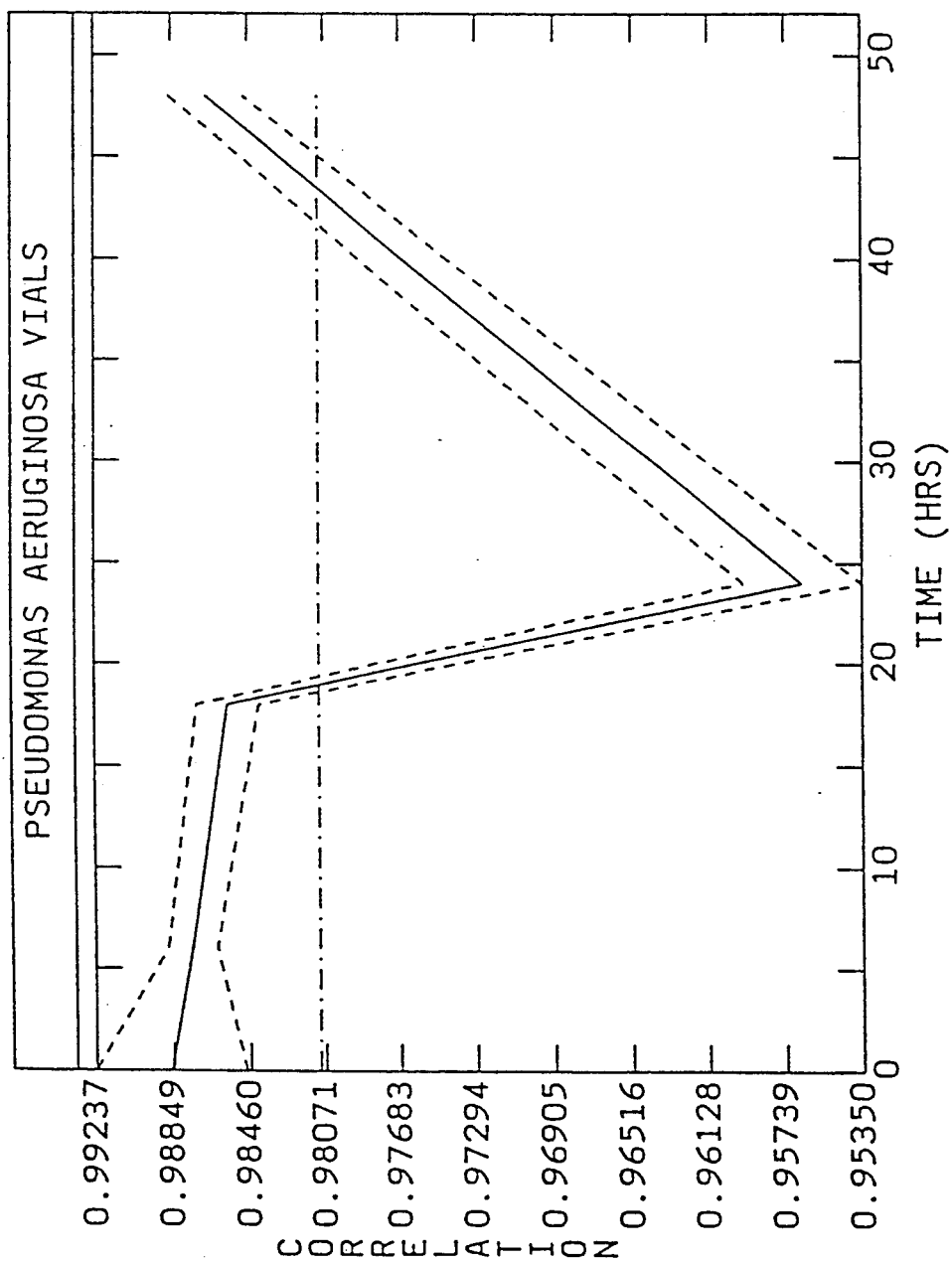
FIG. 17 is a spectra plot of *Pseudomonas aeruginosa* vials over time.
Figure 18:
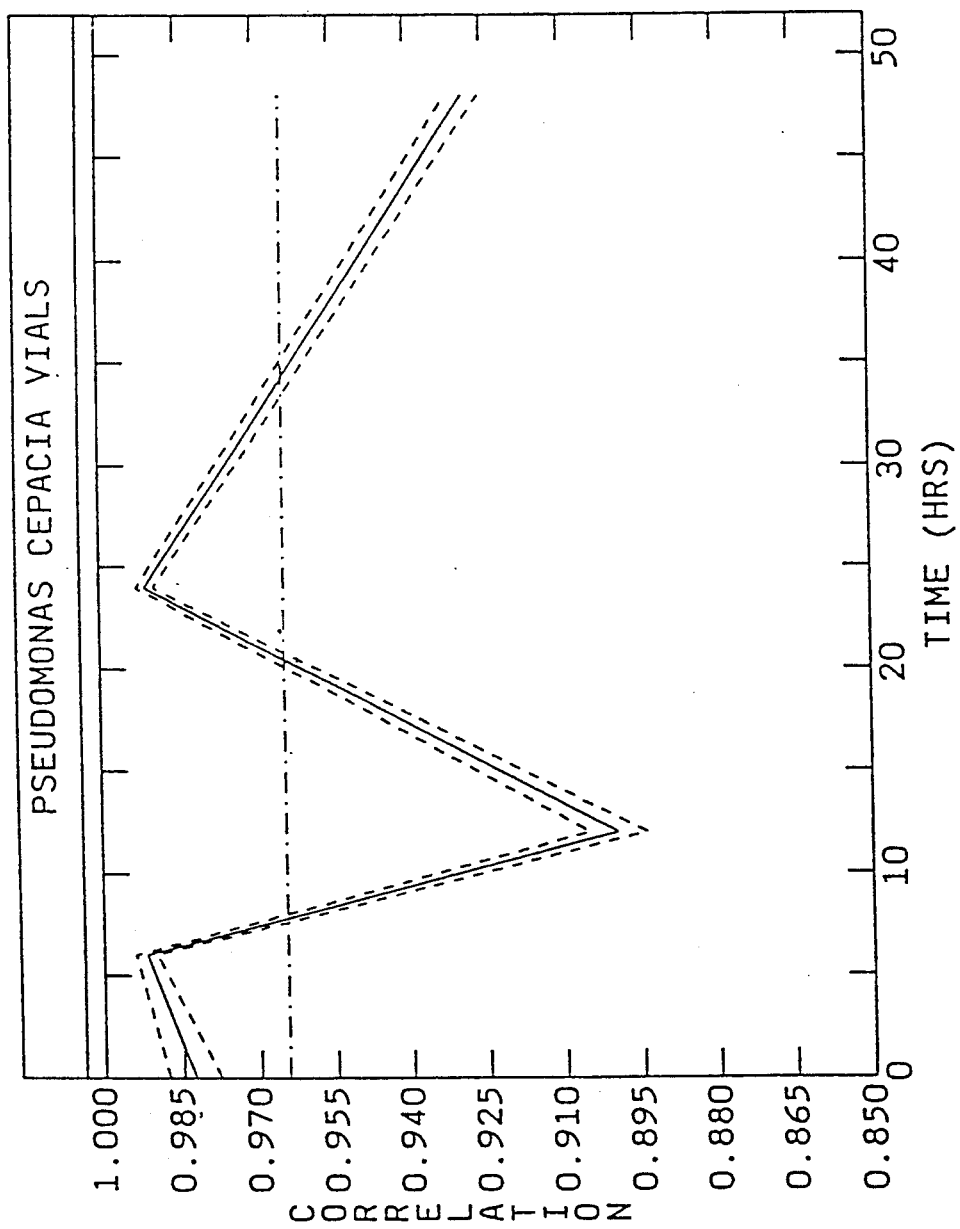
FIG. 18 is a spectra plot of *Pseudomonas cepacia* vials over time.
Figure 19:
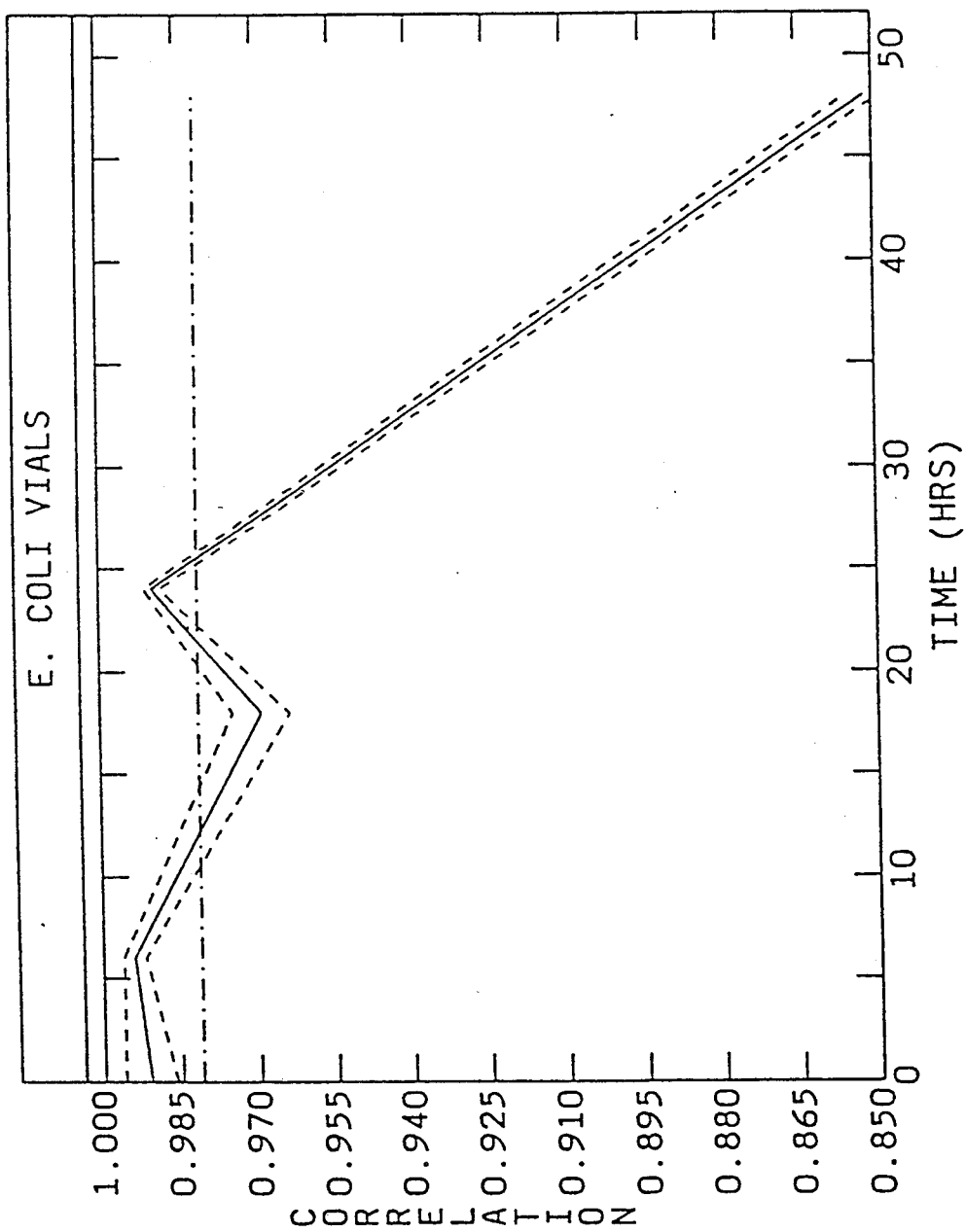
FIG. 19 is a spectra plot of *Escherichia coli* vials over time.

FIG. 17 graphs the change in spectra of the Pseudomonas aeruginosa vials with time. These vials cross the 98% level about 19 hours after injection with 10-100 cfu. Interestingly, the spectra begin to resemble the time=0 spectra again after approximately 43 hours. The rise in Pseudomonas aeruginosa correlations is similar to that reported for Pseudomonas aeruginosa in PVC administration bags (Example 1). It appears that the growth rate of Pseudomonas aeruginosa is different in vials; however, this difference in growth is probably due to differences in the media used in the vial and bag studies and to differences in the optical collection efficiency.

FIG. 7 shows the change in the spectra of Pseudomonas cepacia vials with time. The vials cross the 98% level initially about 8 hours after injection of 10-100 cfu. The correlation does not continue to fall with time, however, and the vials begin to resemble the time=0 spectra again after 20 hours. However, after 34 hours the vial spectral cross the 98% confidence level again. This double-crossing of the confidence limit was also observed in E. coli vials (see FIG. 8). E. coli crossed the 98% confidence level initially approximately 12 hours after injection of 10-100 cfu. The vials resembled the time=0 spectra for a short period from 22 to 26 hours after the injection of bacteria. Beyond 26 hours after injection the vials apparently stayed below the 98% correlation confidence level.

In a related study employing Candida albicans in PVC administration bags, the correlation of spectra to time 0 values was monitored continuously, and the first time the correlation dropped below the 98% confidence level, the media was withdrawn from the bags into new bags through a 0.2 μm filter. Fresh media was then backflushed into the original bags, carrying with it all of the solid material from the filter. In this way, the solid material (cells, etc.) from the original bags was separated from the solution. When the solid material bags were compared to the time=0 bag spectra, the bags containing the cells and solid material were identical at the 98% level to the time=0 bags. The bags containing the solution from the original bags, however, were different from the time=0 bag spectra at the 98% level, indicating that the earliest changes observed in bag spectra are due to changes in the composition of the solution in the bags, and not to an increase in scattered light from cells in solution.

The double-crossing of the 98% confidence level may therefore represent a change in the physical mechanism at the source of the spectral changes observed by the near-IR macroscopic technique. The first crossing may occur when changes in the composition of the solutions alter the transmission spectra of the bags. As the number of cells increases in the bags, the number of scattering events per unit volume increases, shortening the average pathlength and weakening the effect of solution changes on the observed spectra, (hence, the spectra recorded at later times may begin to resemble the spectra recorded at time=0). Finally, as cells continue to proliferate, the spectral contribution of light scattered by cells may become significant in the observed spectra, and the drop in correlation between time=0 spectra and later spectra may being again. These results indicate that the present near-IR method of vial inspection is able to detect changes in the composition of sealed vials.

| Abbreviations | |
|---|---|
| IV | intravenous |
| PVC | polyvinyl chloride |
| mL | milliliters |
| nm | nanometers |
| QQ | quantile-quantile |
| CDF | Cumulative Distribution Functions |
| near-IR | near infrared radiation |
| cfu | colony forming units |

-continued

| | |
|---|---|
| mg | milligrams |
| FDA | U.S. Food and Drug Administration |
| USP | United States Pharmacopeia |
| ATCC | American Type Culture Collection |
| hrs | hours |
| eq | equation |

LIST OF SYMBOLS
Special defined operations:

| | |
|---|---|
| W | linear ("moving average") smoothing |
| $d(f(x))/dx$ | derivative of $f(x)$ |
| $\underline{M}(f(x),x)$ | $x \ (d(f(x))/dx) = 0 \land (d^2(f(x))/dx^2) < 0$ |
| r | random number on $0 < x < 1$; Monte Carlo integration of continuous uniform distribution |
| $\kappa(Z)$ | creates a bootstrap distribution containing m elements for a set of real samples, and find the center of this bootstrap distribution |
| $[x]$ | the greatest-integer function of a scalar, matrix, or array |
| $\partial(x)$ | ordered elements of x (x is a matrix or array) |
| = | equals, or "is replaced by" when the same variable appears on both sides of = |
| $\underline{S}$ | spectral estimator (filter) based on cubic splines |

Scalars:

| | |
|---|---|
| n | the training-set, test-set, and validation-set size, i.e., the number of samples that the set contains |
| d | the number of wavelengths and the dimensionality of the analytical space |
| m | the number of sample set replications forming a bootstrap distribution (user-determined) |
| i | an index for counting rows in a matrix or array |
| j | an index for counting columns in a matrix or array |
| $n_h$ | the number of replicate spectral points falling inside a hypercylinder |
| p | proportion of a distance distribution to trim from each end of the distribution |
| $t_L$ | tolerance value on spectral estimation |
| $\Delta$ | wavelength increment |
| $\tau$ | random number on interval $[0 \leq \tau < 1]$ |
| u | the number of spectra collected from a single sample bag |
| w | the number of wavelengths collected from a single sample bag |
| $s_I$ | an index marker for a wavelength region of interest |
| $p_1$ | the index number of a spectrum showing the greatest overall signal in a set of u spectra |
| $p_2$ | the index number of a spectrum showing the greatest analytical signal over a wavelength region of interest in a set of u spectra |
| $\phi$ | the difference between the absorbances of two spectra from a single bag at the lowest wavelength |

Matrices, vectors, and arrays:

| | |
|---|---|
| $N_{(m)} = (n_{(m)j})_w$ | wavelength vector recorded by spectrometer |
| $I_{(dI)} = (i_{(dI)ij})_{u,w}$ | first derivatives of all spectra collected from a single bag |
| $I_{(1)} = (i_{(1)ij})_{u,w}$ | smoothed set of u spectra collected from a single bag |
| $I = (i_{ij})_{u,w}$ | set of u spectra as collected from a single bag |
| $I_{(d2)} = (i_{(d2)ij})_{u,w-s_I}$ | first derivative of region of interest |
| $I_{(s1)} = (i_{(s1)i})_u$ | sum of absolute value of first derivative of full spectra |
| $I_{(s2)} = (i_{(s2)i})_u$ | sum of absolute value of first derivative of wavelength region of spectral interest |
| $H_{(1)} = (h_j)_w$ | spectrum selected by the index $p_1$ |
| $H_{(2)} = (h_j)$ | spectrum selected by the index $p_2$ |
| $B = (b_{ij})_{m,d}$ | m-by-d bootstrap distribution of training-set sample spectra |
| $B_{(X)} = (b_{ij})_{m,d}$ | bootstrap distribution of test-set sample spectra |
| $B_{(V)} = (b_{ij})_{m,d}$ | bootstrap distribution of validation-set sample spectra |
| $C = (c_j)_d$ | center of the bootstrap distribution B |
| $P = (p_{ij})_{m,n}$ | training-set sample numbers selected for the bootstrap-sample sets used to calculate bootstrap distribution |
| $W = (w_j)_d$ | wavelength at which signals are recorded |
| $W_i = (w_{ij})_d$ | wavelengths at which signals are estimated by filter $\underline{S}$ |
| $Y = (y_{ij})_{n,d}$ | signals recorded from n vials at d wavelengths |
| $\delta = (\delta_{ij})_{n,d}$ | estimated errors (in SDs) of the signals recorded in Y |
| $T = (t_{ij})_{n,d}$ | training-set sample spectra |
| $X = (x_{ij})_{n,d}$ | test-set sample spectra |
| $V = (v_{ij})_{n,d}$ | validation-set sample spectra |
| $K = (k_j)_n$ | training-set sample numbers selected for a particular bootstrap sample |
| $B_{(s)} = (b_{(s)ij})_{n,d}$ | bootstrap sample set used to calculate single rows of a bootstrap distribution (B, $B_{(X)}$, or $B_{(V)}$) |
| $S_{(T)} = (s_{(T)i})_m$ | Euclidean distances of training-set replicates from C, the center of the bootstrap distribution of the training set |
| $S_{(X)} = (s_{(X)i})_m$ | Euclidean distances of test-set replicates from C |
| $S_{(V)} = (s_{(V)i})_m$ | Euclidean distances of validation-set replicates from C |
| $P_{(T)} = (p_i)_{m-2pm}$ | set of (m-2pm) indices used for trimming distance distributions |
| $C_{(t)} = (c_{(t)i})_{2m-4pm}$ | cumulative distribution function (CDF) formed by the trimmed and ordered elements of the training-set bootstrap distribution; CDF has (2m-4pm) elements |
| $C_{(X)} = (c_{(X)i})_{2m-4pm}$ | CDF formed by the trimmed and ordered elements of the test-set and training-set bootstrap distributions |
| $C_{(V)} = (c_{(V)i})_{2m-4pm}$ | CDF formed by the trimmed and ordered elements of the validation-set and training-set bootstrap distributions |

I claim:

1. An apparatus for the noninvasive and non destructive detection of a microorganism with a liquid product contained within a vial, comprising:
   a light source for producing an incident beam;
   means for directing said incident beam through said vial and liquid product;
   means for reflecting said incident beam through said vial and liquid product;
   means for detecting the reflected incident beam and light scattered by any microorganisms present in said liquid product; and
   means for analyzing said incident beam and light scattered by any microorganism that is detected.

2. The apparatus set forth in claim 1 wherein said light source produces an incident beam having a wavelength between 800 and 2500 nm.

3. The apparatus set forth in claim 1, wherein said light source produces an incident beam having a wavelength between 1100 and 1360 nm.

4. The apparatus set forth in claim 1, wherein said light source also produces a reference beam that is directed to said detecting means so as to compensate for noise and source intensity variations.

5. The apparatus set forth in claim 1, further including an integrating sphere for collecting scattered light and directing said scattered light toward said detecting means.

6. The apparatus set forth in claim 5, wherein said integrating sphere includes an incident beam port and a sample window opposite said incident beam port through which said incident beam is directed at said vial and said liquid product.

7. The apparatus set forth in claim 6, wherein said detecting means is mounted within said integrating sphere adjacent said sample window.

8. The apparatus set forth in claim 7, wherein said integrating sphere further includes a reference beam port.

9. The apparatus set forth in claim 8, wherein said reflecting means comprises a substantially U-shaped mirror.

10. The apparatus set forth in claim 9, wherein said sample window of said integrating sphere is positioned along the open end of said substantially U-shaped mirror.

11. The apparatus set forth in claim 10, wherein said sample window positioned along the open end of said substantially U-shaped mirror is also adjacent a sidewall of said substantially U-shaped mirror.

12. A method for the noninvasive and nondestructive detection of a microorganism within a liquid product contained with a vial, comprising the steps of:

placing the vial adjacent a mirror;

directing an incident beam of light into said vial and liquid product;

detecting said incident beam of light as well as light scattered by any microorganism present in the liquid product following reflection by said mirror; and analyzing said incident beam and light scattered by any microorganism that is detected.

13. The method set forth in claim 12, wherein said mirror is substantially U-shaped and has a cavity sized to receive said vial.

14. The method set forth in claim 13, wherein said incident beam is directed into said vial through an open end of said substantially U-shaped mirror adjacent a sidewall of said mirror.

15. The method set forth in claim 12, including reflecting said incident beam through said vial and liquid product at least twice before detecting.

16. The method set forth in claim 12, including reflecting said incident beam through said vial and liquid product at least three times before detecting.

17. The method set forth in claim 12, including steps of identifying multiple discrete scanning planes through said vial and liquid product and directing said incident beam through said multiple discrete scanning planes in order to detect a microorganism in said liquid product.

18. The method set forth in claim 12, including providing a reference beam to compensate for noise and source-intensity variations.

19. The method set forth in claim 12, wherein said incident beam has a wavelength between 1100 and 1360 nm.

* * * * *